United States Patent
Foody et al.

(10) Patent No.: US 10,995,314 B2
(45) Date of Patent: May 4, 2021

(54) SULFUR DIOXIDE AND/OR SULFUROUS ACID PRETREATMENT WITH SULFUR DIOXIDE RECOVERY

(71) Applicant: Iogen Corporation, Ottawa (CA)

(72) Inventors: Brian Foody, Ottawa (CA); Daniel G. MacDonald, Orleans (CA); Kristin Martens, Nepean (CA); Natacha Leduc, Hammond (CA); John Dechman, Ottawa (CA); Robert Griffin, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

(21) Appl. No.: 15/550,582

(22) PCT Filed: Mar. 16, 2016

(86) PCT No.: PCT/CA2016/050292
§ 371 (c)(1),
(2) Date: Aug. 11, 2017

(87) PCT Pub. No.: WO2016/145531
PCT Pub. Date: Sep. 22, 2016

(65) Prior Publication Data
US 2018/0037863 A1    Feb. 8, 2018

Related U.S. Application Data

(60) Provisional application No. 62/269,339, filed on Dec. 18, 2015, provisional application No. 62/142,068, filed on Apr. 2, 2015, provisional application No. 62/133,609, filed on Mar. 16, 2015.

(51) Int. Cl.
| | | |
|---|---|---|
| *C12M 1/00* | (2006.01) | |
| *C12P 19/02* | (2006.01) | |
| *C12P 19/14* | (2006.01) | |
| *C12P 7/10* | (2006.01) | |
| *D21C 1/02* | (2006.01) | |
| *D21C 1/04* | (2006.01) | |
| *D21C 3/06* | (2006.01) | |
| *B01D 53/00* | (2006.01) | |
| *C12P 7/14* | (2006.01) | |
| *B01D 53/50* | (2006.01) | |
| *B01D 53/14* | (2006.01) | |

(52) U.S. Cl.
CPC .......... *C12M 45/03* (2013.01); *B01D 53/002* (2013.01); *B01D 53/1481* (2013.01); *B01D 53/501* (2013.01); *C12M 45/09* (2013.01); *C12M 45/20* (2013.01); *C12P 7/10* (2013.01); *C12P 7/14* (2013.01); *C12P 19/02* (2013.01); *C12P 19/14* (2013.01); *C12Y 302/01004* (2013.01); *D21C 1/02* (2013.01); *D21C 1/04* (2013.01); *D21C 3/06* (2013.01); *B01D 2251/60* (2013.01); *B01D 2252/10* (2013.01); *B01D 2252/102* (2013.01); *B01D 2257/302* (2013.01); *C12P 2201/00* (2013.01); *C12P 2203/00* (2013.01); *Y02E 50/10* (2013.01)

(58) Field of Classification Search
CPC ...... C12M 45/03; C12M 45/09; C12M 45/20; B01D 53/002; B01D 53/1481; B01D 53/501; B01D 2251/60; B01D 2252/10; B01D 2252/102; B01D 2257/302; C12P 7/10; C12P 7/14; C12P 19/02; C12P 19/14; C12P 2201/00; C12P 2203/00; C12Y 302/01004; D21C 1/02; D21C 1/04; D21C 3/06; Y02E 50/10
USPC ...................................................... 424/93.1
See application file for complete search history.

(56) References Cited

U.S. PATENT DOCUMENTS

| | | |
|---|---|---|
| 2,418,167 A | 4/1947 | Du Bois |
| 5,424,417 A | 6/1995 | Torget et al. |
| 5,789,210 A | 8/1998 | Ho et al. |
| 5,866,382 A | 2/1999 | Hallborn et al. |
| 6,475,768 B1 | 11/2002 | Otero et al. |
| 6,582,944 B1 | 6/2003 | Hallborn et al. |
| 7,527,927 B1 | 5/2009 | Ho et al. |
| 7,527,951 B2 | 5/2009 | Londesborough et al. |
| 7,585,652 B2 | 9/2009 | Foody et al. |
| 7,622,284 B2 | 11/2009 | Op Den Camp et al. |
| 7,754,456 B2 | 7/2010 | Penttila et al. |

(Continued)

FOREIGN PATENT DOCUMENTS

| | | |
|---|---|---|
| WO | 2006/034590 A1 | 4/2006 |
| WO | 2006/034591 A1 | 4/2006 |
| WO | 2006/128304 A1 | 12/2006 |
| WO | 2008/041840 A1 | 4/2008 |
| WO | 2010/022511 A1 | 3/2010 |

(Continued)

OTHER PUBLICATIONS

Kumar et al., Effects of Cellulase and Xylanase Enzymes on the Deconstruction of Solids from Pretreatment of Poplar by Leading Technologies, Biotechnol. Prog., vol. 25, No. 2, (2009) pp. 302-314.*

(Continued)

*Primary Examiner* — Jennifer M. H. Tichy
(74) *Attorney, Agent, or Firm* — Knobbe Martens Olson & Bear, LLP

(57) ABSTRACT

A process for producing ethanol from lignocellulosic biomass includes adding at least one of sulfur dioxide and sulfurous acid to the lignocellulosic biomass to provide an equivalent sulfur dioxide loading of at least 10 wt % sulfur dioxide to dry lignocellulosic biomass. The acidified lignocellulosic biomass is pretreated at a temperature above about 185° C. and for a pretreatment time less than about 10 minutes, to provide a pretreated biomass composition wherein the biomass is readily hydrolyzed by enzymes. Advantageously, sulfur dioxide from at least one of the flash stream and a stream derived from the flash is recovered and recycled back into the process.

27 Claims, 8 Drawing Sheets

(56) References Cited

U.S. PATENT DOCUMENTS

| | | | |
|---|---|---|---|
| 8,038,842 | B2 | 10/2011 | Retsina et al. |
| 8,268,125 | B2 | 9/2012 | Retsina et al. |
| 8,409,836 | B2 | 4/2013 | Vehmaanpera et al. |
| 8,709,770 | B2 | 4/2014 | Harlick et al. |
| 8,728,243 | B2 | 4/2014 | van der Meulen et al. |
| 8,815,499 | B2 | 8/2014 | Alriksson et al. |
| 8,815,561 | B2 | 8/2014 | Liu et al. |
| 8,834,633 | B2 | 9/2014 | van der Meulen et al. |
| 8,871,475 | B2 | 10/2014 | Alriksson et al. |
| 9,012,188 | B2 | 4/2015 | Van Heiningen et al. |
| 9,068,236 | B2 | 6/2015 | Heikkila et al. |
| 9,090,915 | B2 | 7/2015 | Wang et al. |
| 9,102,951 | B2 | 8/2015 | Griffin et al. |
| 9,290,821 | B2 | 3/2016 | Blackbourn et al. |
| 9,574,212 | B2 | 2/2017 | Foody et al. |
| 9,738,729 | B2 | 8/2017 | Retsina et al. |
| 2006/0068475 | A1* | 3/2006 | Foody .................. C12P 7/10 435/105 |
| 2007/0254348 | A1 | 11/2007 | Retsina et al. |
| 2009/0118477 | A1 | 5/2009 | Hallberg et al. |
| 2010/0056774 | A1 | 3/2010 | Anand et al. |
| 2010/0279361 | A1 | 11/2010 | South et al. |
| 2011/0165643 | A1* | 7/2011 | Retsina .................. D21C 3/20 435/157 |
| 2011/0300586 | A1 | 12/2011 | Liu et al. |
| 2012/0041186 | A1 | 2/2012 | Pschorn et al. |
| 2012/0052534 | A1 | 3/2012 | Harlick et al. |
| 2012/0073199 | A1 | 3/2012 | Lewis |
| 2012/0237983 | A1 | 9/2012 | Harlick |
| 2013/0071903 | A1 | 3/2013 | Rowland et al. |
| 2014/0034047 | A1* | 2/2014 | Retsina .................. C08B 1/00 127/37 |
| 2014/0053827 | A1 | 2/2014 | Baudel et al. |
| 2014/0142351 | A1 | 5/2014 | Johnston et al. |
| 2014/0154746 | A1 | 6/2014 | Jonsson et al. |
| 2014/0163210 | A1 | 6/2014 | Retsina et al. |
| 2014/0178944 | A1 | 6/2014 | Parekh et al. |
| 2014/0182582 | A1 | 7/2014 | Retsina et al. |
| 2014/0186899 | A1 | 7/2014 | Retsina et al. |
| 2014/0186903 | A1* | 7/2014 | Retsina .................. C07C 51/09 435/126 |
| 2015/0259709 | A1 | 9/2015 | Retsina et al. |
| 2016/0257979 | A1 | 9/2016 | Restina et al. |
| 2016/0281298 | A1 | 9/2016 | Nelson et al. |
| 2017/0002387 | A1 | 1/2017 | Retsina et al. |

FOREIGN PATENT DOCUMENTS

| | | |
|---|---|---|
| WO | 2013/113579 A1 | 8/2013 |
| WO | 2014/106222 A2 | 7/2014 |
| WO | 2016/145527 A1 | 9/2016 |
| WO | 2016/145528 A1 | 9/2016 |
| WO | 2016/145529 A1 | 9/2016 |
| WO | 2016/145530 A1 | 9/2016 |

OTHER PUBLICATIONS

Shevchenko et al., "Optimization of monosaccharide recovery by post-hydrolysis of the water-soluble hemicellulose component after steam explosion of softwood chips," 2000, Bioresource Technology, pp. 207-211, vol. 72.

Shevchenko et al., "The Nature of Lignin from Steam Explosion/Enzymatic Hydrolysis of Softwood," 1999, Applied Biochemistry and Biotechnology, pp. 867-876, vol. 77-79.

Shi et al,, "Sugar yields from dilute sulfuric acid and sulfur dioxide pretreatments and subsequent enzymatic hydrolysis of switchgrass," 2011, Bioresource Technology, pp. 8930-8938, vol. 102.

Shuai et al., "Comparitive study of SPORL and dilute-acid pretreatments of spruce for cellulosic ethanol production," 2010, Bioresource Technology, pp. 3106-3114, vol. 2010.

Sipos et al., "Steam pretreatment of dry and ensiled industrial hemp for ethanol production," 2010, Biomass and Bioenergy, pp. 1-11.

Soderstrom et al. "Effect of Washing on Yield in One- and Two-Step Steam Pretreatment of Softwood for Production of Ethanol," 2004, Biotehncol, Prog., pp. 744-749, vol. 20.

Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.

Soderstrom et al. "Two-Step Steam Pretreatment of Softwood with SO2 impregnation for Ethanol Production," 2002, Applied Biochemistry and Biotechnology, pp. 5-21, vol. 98-100.

Szengyel et al., "Cellulase Production of Trichoderma reesei Rut C 30 Using Steam-Penetrated Spruce," 2000, Applied Biochemistry and Biotechnology, pp. 679-691, vol. 84-86.

Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.

Tengborg et al., "Reduced inhibition of enzymatic hydrolysis of steam-pretreated softwood," 2001, Enzyme and Microbial Technology, pp. 835-844, vol. 28.

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain *Saccharomyces cerevisiae* without detoxification," 2010, Bioresource Technology, pp. 8678-8685, vol. 101.

Trajano et al, "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergetic effects of mixing hybrid poplar and wheat straw biomass for bioconversion processes," 2015, Biotechnol Biofuels, pp. 1-10, vol. 8:226.

Von Sivers et al., "A Techno-Econornical Comparison of Three Processes for the Production of Ethanol from Pine," 1995, Bioresource Technology, pp. 43-52, vol. 51.

Wang et al., "Lignosulfonate and elevated pH can enhance enzymatic saccharification of lignocelluloses," 2013, Biotechnology for Biofuels, pp. 1-10, vol. 6:9.

Wang et al., "Ethanol production from poplar wood through enzymatic saccharification and fermentation by dilute acid and SPORL pretreatrnents," 2012, Fuel, pp. 606-614, vol. 95.

Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.

Wayman et al., "Hydrolysis of Biomass by Sulphur Dioxide," 1984, Biomass, pp. 183-191, vol. 6.

Wayman et al., "SO2 Catalysed Prehydrolysis of Coniferous Wood for Ethanol Production," 1986, Biotechnology Letters, pp. 749-752, vol. 8, No. 10.

Wiman et al., "Cellulose accessibility determines the rate of enzymatic hydrolysis of steam-pretreated spruce," 2012, Bioresource Technology, pp. 208-215, vol. 126.

Wolfinger et al., "Modeling of the Acid Sulfite Pulping Process—Problem Definition and Theoretical Approach for a solution with the Main Focus on the Recovery of Cooking Chemicals," 2004, Lenzinger Berichte, pp. 35-45, vol. 83.

Wooley, Bob, "Production of 1,000 Gallons of BioJet," 2015, Presentation from 2015 Annual Meeting of Northwest Advanced Renewables Alliance (NARA).

Wyman et al., "Comparative data on effects of leading pretreatments and enzyme loadings and formulations on sugar yields from different switchgrass sources," 2011, Bioresource Technology, 11052-11062, vol. 102.

Wyman et al., "Comparitive Sugar Recovery and Fermentation Data Following Pretreatment of Poplar Wood by Leading Technologies," 2009, Biotechnol. Prog., pp. 333-339, vol. 25, No. 2.

Fan et al., "Optimization of SO2-catalyzed hydrolysis of corncob for xylose and xylitol production," 2014, J Chem Technol Biotechnol, pp. 1720-1726, vol. 89.

(56) References Cited

OTHER PUBLICATIONS

Zhang et al., "Sulfite (SPORL) pretreatment of switchgrass for enzymatic saccharification," 2013, Bioresource Technology, pp. 127-134, vol. 129.
Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.
Zhu et al., "Woody biomass pretreatment for cellulosic ethanol production: Technology and energy consumption evaluation," 2010, Bioresource Technology, pp. 4992-5002, vol. 101.
Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.
Zhu et al., "Ethanol production from SPORL-pretreated lodgepole pine: preliminary evaluation of mass balance and process energy efficiency," 2010, Appl Microbiol Biotechnol, pp. 1355-1365, vol. 86.
Zhu et al., "High Titer Ethanol Production from Forest Residue Using Sulfite Mill Pulping Chemistry," 2015, Presentation at 2015 TAPPI IBBC.
Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.
Zhu et al., "On Polydispersity of Plant Biomass Recalcitrance and its Effects on Pretreatment Optimization for Sugar Production," 2011, Bioenerg. Res., pp. 201-210, vol. 4.
Zhu et al., Quantitative predictions of bioconversion of aspen by dilute acid and SPORL pretreatments using a unified combined hydrolysis factor (CHF), 2012, Process Biochemistry, pp. 785-791, vol. 47.
Zhu et al., "Sulfite pretreatment (SPORL) for robust enzymatic saccharification of spruce and red pine," 2009, Bioresource Technology, pp. 2411-2418, vol. 100.
Hakka et al., "Recovery and recycling of SO2 in a sulfite pulp mill," 1998.
Larue et al., "Sulfur plant configurations for weird acid gases", 2013, Laurance Reid Gas Conditioning Conference.
Tao et al., "Process and technoeconomic analysis of leading pretreatment technologies for lignocellulosic ethanol production using switchgrass," 2011, Bioresource Technology, pp. 11105-11114, vol. 102.
Cavka et al., "Identification of small aliphatic aldehydes in pretreated lignocellulosic feedstocks and evaluation of their inhibitory effects on yeast", 2015, J. Agric. Food Chem., 63, 9747-9754.
Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.
Schell et al., "Pretreatment of Softwood by Acid-Catalyzed Steam Explosion Followed by Alkali Extraction," 1998, Applied Biochemistry and Biotechnology, pp. 17-24, vol. 70-72.
Schwald et al., "Assessment of Pretreatment Conditions to Obtain Fast Complete Hydrolysis on High Substrate Concentrations," 1989, Applied Biochemistry and Biotechnology, pp. 29-44, vol. 21/21.
Sendelius et al., "Steam Pretreatment Optimisation for Sugarcane Bagasse in Bioethanol Production," 2005, Master of Science Thesis, Lund University, Sweden.
Bensah, E. and Mensah, M., "Chemical Pretreatment Methods for the Production of Cellulosic Ethanol: Technologies and Innovations," International Journal of Chemical Engineering, 2013, pp. 1-21, vol. 2013.
Bhalla, A. et al., "Improved lignocellulose conversion to biofuels with thermophilic bacteria and thermostable enzymes," Bioresource Technology, 2013, pp. 751-759, vol. 128.

Boussaid, A., et al., "Fermentability of the Hemicellulose-Derived Sugars from Steam-Exploded Softwood (Douglas Fir)," , Biotechnology and Bioengineering, 1999, pp. 284-289, vol. 64, No. 3.
Brownell, H. and Saddler, J., "Steam Pretreatment of Lignocellulosic Material for Enhanced Enzymatic Hydrolysis," Biotechnology arid Bioengineering, 1987, pp. 228-235, vol. 29.
Bura, et al., "Moving towards commercialization of lignoceiiulosic biomass to fuels to chemicals. How to deal with heterogeneous biomass?" University of Washington Biofuels and Bioproducts Laboratory, 2012.
Bura, R., et al., "Influence of Xylan on the Enzymatic Hydrolysis of Steam-Pretreated Corn Stover and Hybrid Poplar," Biotechnol Prog, 2009, pp. 315-322, vol. 25, No. 2.
Bura, R., et al., "SO2-Catalyzed Steam Explosion of Corn Fiber for Ethanol Production", Applied Biochemistry and Biotechnology, 2002, pp. 59-72, vols. 98-100.
Carrasco, C., et al., "SO2-catalysed steam pretreatment of quinoa stalks," J Chem Technol Biotechnol, 2015, pp. 64-71, vol. 90.
Carrasco, C., et al., "SO2-catalyzed steam pretreatment and fermentation of enzymatically hydrolyzed sugarcane bagasse," Enzyme and Microbial Technology, 2010, pp. 64-73, vol. 46.
Carrasco, C., "Arabinosylated phenolics obtained from SO2-steam-pretreated sugarcane bagasse," Journal of Chemical Technology and Biotechnology, 2012, pp. 1723-1726, vol. 87.
Chacha, N., et al., "Steam Pretreatment of Pine (Pinus patula) Wood Residue for the Production of Reducing Sugars," Cellulose Chemistry and Technology, 2011, pp. 495-501, vol. 45 (7-8).
Chandra, R., et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Clark, T.A. et al., "Steam Explosion of the Softwood Finns Radiata with Sulphur Dioxide Addition. II. Process Characterisation," Journal of Wood Chemistry and Technology, 1989, pp. 135-166, vol. 9:2.
Clark, T.A. et al., "Steam Explosion of the Softwood Pinus Radiata with Sulphur Dioxide Addition. I. Process Optimization," Journal of Wood Chemistry and Technology, 1987, pp. 373-403, vol. 7:3.
Corrales et al., "Structural evaluation of sugar cane bagasse steam pretreated in the presence of CO2 and SO2," Biotechnology for Biofuels, 2012, pp. 1-8, vol. 5:36.
De Bari et al., "SO2-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H., et al., "Enzymic Saccharification of Sugarcane Bagasse Pretreated by Autohydroiysis-Steam . Explosion," Biotechnology and Bioengineering, 1983, pp. 3027-3048, vol. XXV.
Dekker, Robert F. H., "The Utilization of Autohydrolysis-Exploded Hardwood (Eucalyptus Regnans) and Softwood (Pinus Radiata) Sawdust for the Production of Cellulolytic Enzymes and Fermentable Substrates," Biocatalysis, 1987, pp. 63-75, vol. 1.
Ehsanipour, Mandana "Bioconversion of lignocelluiosic hydrolysate to acetic acid using Moorella thermoacetica," a thesis submitted in partial fulfillment of the requirements for the degree of Master of Science at University of Washington, 2015.
Eklund et al., "The Influence of SO2 and H2SO4 Impregnation of Willow Prior to Steam Pretreatment," 1995, Bioresource Engineering, pp. 225-229. vol. 52.
Elander, et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Galbe et al., "A review of the production of ethanol from softwood," 2002, Appl Microbial Biotechnol, pp. 618-628, vol. 59.
Garlock et al., "Comparative material balances around pretreatment technologies for the conversion of switchgrass to soluble sugars," 2011, Bioresource Technology, pp. 11063-11071, vol. 102.

(56) References Cited

OTHER PUBLICATIONS

Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.

Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.

Hodge et al., "Soluble and insoluble solids contributions to high-solids enzymatic hydrolysis of lignocellulose," 2008, Bioresource Technology, pp. 8940-8948, vol. 99.

Hodge et al., "Soluble and insoluble solids contributions to high-solids enzymatic hydrolysis of lignocellulose," 2006, Bioresource Technology, pp. 8940-8948, vol. 99.

Kumar et al., "Access of Cellulase to Cellulose and Lignin for Poplar Solids Produced by Leading Pretreatment Technologies," 2009, Biotechnol. Prog., pp. 807-819, vol. 25, No. 3.

Lan et al., "High titer ethanol production from SPORL-pretreated lodgepole pine by simultaneous enzymatic saccharification and combined fermentation," 2013, Bioresource Technology, pp. 291-297, vol. 127.

Leu et al., "Substrate-Related Factors Affecting Enzymatic Saccharification of Lignocelluloses; Our Recent Understanding," 2013, Bioenerg. Res., pp. 405-415, vol. 6.

Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).

Mackie et al., "Effect of Sulphur Dioxide and Sulphuric Acid on Steam Explosion of Aspenwood," 1985, Journal of Wood Chemistry and Technology, pp. 405-425, vol. 5(3).

Mamers et al., "Explosion pretreatment of Pinus radiata woodchips for the production of fermentation substrates," 1984, Apita, pp. 644-649, vol. 37.

Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.

Monavari et al., "Improved One-Step Steam Pretreatment if SO2-Impregnated Softwood with Time-Dependant Temperature Profile for Ethanol Production," 2010, Biotechnol. Prog., pp. 1054-1060, vol. 26, No. 4.

Nguyen et al., "Dilute Acid Pretreatment of Softwoods," 1998, Applied Biochemistry and Biotechnology, pp. 77-89, vol. 70-72.

Nguyen et al., "Two-Stage Dilute Acid Pretreatment of Softwoods," 2000, Applied Biochemistry and Biotechnology, 561-576, vol. 84-86.

Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.

Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.

Rakkolainen et al., "SO2-Ethanol-Water Fractionation of Forest Biomass and Implications for Biofuel Production by Abe Fermentation," 2010, Cellulose Chem. Technol., pp. 19-145, vol. 44.

Ramos et al. "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.

Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.

Ramos et al., "Effect of enzymatic hydrolysis on the morphology and fine structure of pretreated cellulosic residues," 1993, Enzyme Microb. Technol., pp. 821-831, vol. 15.

Sassner et al., "Steam Pretreatment of Salix with and without SO2 Impregnation for Production of Bioethanol," 2005, Applied Biochemistry and Biotechnology, pp. 1101-1117, vol. 121-124.

International Report on Patentability dated Sep. 19, 2017 for PCT Application No. PCT/CA2016/050292, filed Mar. 16, 2016.

Felby et al., "Ethanol from Wheat Straw Cellulose by Wet Oxidation Pretreatment and Simultaneous Saccharifcation and Fermentation," American Chemical Society, ACS Symposium Series, 2003, pp. 157-174.

\* cited by examiner

SULFUR DIOXIDE AND/OR SULFUROUS ACID PRETREATMENT WITH SULFUR DIOXIDE RECOVERY

CROSS-REFERENCE TO RELATED APPLICATIONS

This application is a national stage application of PCT/CA2016/050292 having an international filing date of Mar. 16, 2016, which claims the priority benefit of provisional application No. 62/133,609, filed Mar. 16, 2015, provisional application No. 62/142,068, filed Apr. 2, 2015, and provisional application No. 62/269,339 filed Dec. 18, 2015, all of which are incorporated herein by reference.

TECHNICAL FIELD

The present disclosure relates to a process for producing ethanol from lignocellulosic biomass, and in particular, to a process comprising sulfur dioxide and/or sulfurous acid pretreatment with sulfur dioxide recovery.

BACKGROUND

The production of transportation fuels (e.g., ethanol) from biomass continues to attract interest, due to the low cost and wide availability of biomass, and because biofuels may be used to displace the use of fossil fuels. For example, ethanol may be blended into gasoline at predetermined concentrations (e.g., 10%).

First generation biofuels, also referred to as conventional biofuels, are made from biomass that contains sugar, starch, or vegetable oil. For example, ethanol may be produced by fermenting sugars that are easily extracted from sugar crops (e.g., sugar cane or sugar beets), or may be produced by fermenting sugars derived from starch-based feedstocks (e.g., corn grain, barley, wheat, potatoes, cassava). In fact, the diversion of farmland or crops for first generation biofuel production has led to much debate about increased food prices and/or decreased food supplies associated therewith. In addition, there are concerns related to the energy and environmental impact of these production processes.

Second generation biofuels, also referred to as advanced biofuels, wherein the biomass contains lignocellulosic material and/or is obtained from agricultural residues or waste (e.g., corn cobs, corn stover (e.g., stocks and leaves), bagasse, wood chips, wood waste), may allay some of these concerns. For example, when bioethanol produced using second generation processes (i.e., also referred to as cellulosic ethanol) is derived from agricultural waste or residue, its production should not affect the food supply. In fact, tremendous effort is currently being expended to advance cellulosic ethanol production processes.

Lignocellulosic biomass typically contains cellulose, hemicellulose and lignin, each of which is present in plant cell walls. Cellulose (e.g., a type of glucan) is an unbranched chain polysaccharide including hexose (C6) sugar monomers (e.g., glucose). Hemicellulose is a branched chain polysaccharide that may include different pentose (C5) sugar monomers (e.g., xylose and arabinose) in addition to glucose. Lignin is a complex organic polymer, which typically includes cross-linked phenol polymers. Although generally insoluble in water at mild conditions, lignin may be soluble in varying degrees in dilute acid or base alkali. The ratio and/or structure of these components may vary depending on the source of the biomass.

The production of ethanol from lignocellulosic biomass most often involves breaking down the cellulose and/or hemicellulose into the constituent sugars, which may then be fermented. Unfortunately, the cellulose, hemicellulose, and/or lignin found in lignocellulosic biomass is typically structured within the plant walls to resist degradation.

Since lignocellulosic biomass is naturally resistant to breakdown into its constituent sugars, a pretreatment step is often used to open up the structure of the material and/or to make it accessible for enzymes used to hydrolyze the cellulosic component. Some examples of pretreatments include dilute acid pretreatment, alkali pretreatment (e.g., lime), ammonia fiber expansion, autohydrolysis (e.g., hot water extraction that does not require the addition of acid or base), steam explosion, organic solvent, and/or wet oxidation.

One type of pretreatment is sulfur dioxide ($SO_2$)-catalyzed steam pretreatment. Sulfur dioxide is a gas, which when dissolved in water, is referred to as a sulfurous acid solution. Sulfur dioxide and/or sulfurous acid may be a suitable catalyst for acid-catalyzed steam pretreatment since it may produce a more digestible substrate and/or may produce less and/or fewer inhibitors and/or inactivators relative to dilute sulfuric acid pretreatment. In addition, sulfur dioxide catalyzed pretreatment may be effective at relatively low temperatures and/or reaction times (e.g., relative to sulfuric acid ($H_2SO_4$) catalyzed pretreatments).

In general, sulfur dioxide pretreatment has been applied to various types of lignocellulosic biomass, including corn stover, bagasse, hardwood, and softwoods. In each case, the sulfur dioxide loading typically has been relatively low. For example, the concentration of sulfur dioxide is typically less than about 10 wt % on dry weight of biomass, and more typically, between about 1 wt % and about 6 wt % on dry weight of biomass. Low acid consumption is often the aim in sulfur dioxide catalyzed steam pretreatments and/or the reason for using sulfur dioxide. For example, one advantage of using sulfur dioxide over sulfuric acid is increased efficiency, which translates to using less acid and thus lower costs, for the same ethanol yield. The combination of using less acid and the fact that sulfur dioxide has a higher pH than sulfuric acid, may provide additional cost savings since less base may be required to adjust the pH of the pretreated material before enzymatic hydrolysis.

Another reason to use a relatively low amount of sulfur dioxide is to design the process such that the severity of the process is within a predetermined range. In general, the severity of pretreatment is dependent on temperature, residence time, and pH, with low severity generally associated with poor improvement of enzymatic hydrolysis and high severity producing a much more digestible cellulose component. The severity of pretreatment reaction may be expressed using a severity factor, log $R_o$, which is defined as:

$$\log(t \cdot e^{(T-100)/14.75}) \qquad (1)$$

where t is the time (in min), and T is the temperature (in ° C.), of the reaction. A combined severity factor (CSF) also takes into account the amount of acid present. For example, the CSF may be calculated from:

$$\log(t \cdot e^{(T-100)/14.75}) - \text{pH} \qquad (2)$$

Although these severity factors do not provide a complete and/or totally accurate prediction of pretreatment efficiency, they do provide at least a rough idea of the approximate pretreatment conditions. For example, as a rough approximation, a 10° C. increase in temperature may have roughly the same impact as doubling the acid concentration or doubling the reaction time.

In general, as the severity of acid-catalyzed pretreatment increases, so does the formation of a large number/amount of by-products that may be inhibitory to fermentation. For example, as the severity increases, so does the production of sugar degradation products such as furfural, which may be derived from C5 sugars (e.g., xylose and arabinose), hydroxymethylfurfural (HMF), which may be derived from C6 sugars (e.g., glucose, mannose, and galactose), and/or acetic acid. Since high severity conditions may degrade sugars (e.g., and thus produce less sugar) and/or produce sugar degradation products that are potential fermentation inhibitors, both of which may reduce ethanol yield, the pretreatment conditions are typically selected to ensure the severity is not too high. In fact, one approach is to design the pretreatment process to maximize the production of xylose during pretreatment (e.g., which may undergo a dehydration to furfural if the combined severity factor is too high). However, since the conventional approach has been to try to achieve the same level of pretreatment with less sulfur dioxide, the sulfur dioxide loading is typically selected to be relatively low while the temperature and/or reaction time are selected accordingly.

Yet another reason for using a relatively low amount of sulfur dioxide is that the sulfur dioxide and/or $SO_2$ recovery may be costly. For example, it has been calculated that dilute sulfuric acid pretreatment is approximately 30% cheaper than sulfur dioxide pretreatment, primarily due to the higher capital cost associated with $SO_2$ recovery (e.g., Schell et al, "A technical and economic analysis of acid-catalyzed steam explosion and dilute sulfuric acid pretreatments using wheat straw or aspen wood chips", Appl. Biochem. Biotechnol. 28/29, 87, 1991).

In WO 2014/106222, there is disclosed a process for fractionating biomass employing sulfur dioxide, wherein a relatively high amount of acid catalyst (e.g., $SO_2$) may be introduced into an organosols type pretreatment (e.g., wherein the solvent is ethanol). The combination of $SO_2$, ethanol, and water, is reported to lead to rapid $SO_2$ impregnation of the biomass and high lignin solubility. However, the use of the ethanol further complicates $SO_2$ recovery (i.e., since ethanol must also be recovered) and requires a relatively long (e.g., between 15 and 720 mins) and low temperature (e.g., between 65° C. and 175° C.) cook. Nevertheless, this type of $SO_2$-ethanol-water (SEW) process has been studied extensively as a fractionation process of lignocellulosic biomass. However, while the SEW process may be useful in the fractionation of lignocellulosic biomass, wherein the primary goal is the clean separation of the different components of lignocellulosic material, it is not ideal for the pretreatment of lignocellulosic material, wherein the primary goal is to open up the cell wall structure and/or to make the cellulose more accessible and/or susceptible to enzymes used to hydrolyze the cellulosic component. In particular, the SEW conditions correspond to a relatively low temperature and long cook times. Moreover, the SEW approach is particularly unsuitable for cellulosic ethanol processes that carry the C5 sugars and/or lignin with the cellulose to enzymatic hydrolysis, as the high ethanol concentration inhibits cellulase.

SUMMARY

The present disclosure describes one or more embodiments wherein sulfur dioxide and/or sulfurous acid is added at a sulfur dioxide concentration selected to be greater than approximately 10% on dry weight of biomass and/or to provide a pH that is less than approximately 1.5. Advantageously, this relatively high sulfur dioxide loading and/or relatively low pH has been found to provide improved pretreatment of the lignocellulosic material for hydrolysis (e.g., increase the responsivity of the cellulose to enzymatic attack). For example, it has been found that when this high sulfur dioxide loading is combined with a pretreatment temperature above about 185° C., the enzyme usage may be at least halved (e.g., relative to a $H_2SO_4$ treatment) for a given ethanol yield. Since the cost of enzymes significantly contributes to the overall process costs, this reduction in enzyme usage translates to significant cost savings. In addition, since this reduction in enzyme usage may be provided when the pretreated lignocellulosic biomass is not washed or substantially unwashed between pretreatment and hydrolysis, additional economic advantages related to process time, simplicity, reduced water usage, high consistency hydrolyses, etc., may be provided. Further cost savings may be achieved by recovering and/or recycling sulfur dioxide from the pretreatment, particularly, by flashing. For example, the relatively high concentration of sulfur dioxide introduced into the pretreatment reactor may allow a large portion of the sulfur dioxide to be recovered and/or recycled quickly and cost effectively.

One aspect of the present disclosure is directed to a process for producing ethanol from lignocellulosic biomass comprising: a) adding acid to lignocellulosic biomass to produce acidified lignocellulosic biomass, said acid comprising at least one of sulfur dioxide and sulfurous acid; b) pretreating said acidified lignocellulosic biomass to produce a pretreated biomass composition comprising cellulose, said pretreating conducted in a pressurized pretreatment reactor at a temperature above about 185° C. and at a pH less than about 1.5; c) reducing a pressure on the pretreated biomass composition to produce a flash stream and a cooled pretreated biomass composition; d) obtaining at least one of sulfur dioxide and sulfurous acid from at least one of the flash stream and a stream derived from the flash stream; e) hydrolyzing cellulose from the cooled pretreated biomass composition in the presence of a cellulase to produce glucose; f) fermenting at least a portion of the glucose to ethanol; and g) recycling the at least one of sulfur dioxide and sulfurous acid derived from step d) back into the process.

One aspect of the present disclosure is directed to a process for producing ethanol from lignocellulosic biomass comprising: a) adding acid and lignocellulosic biomass to a pretreatment reactor, said acid comprising at least one of sulfur dioxide and sulfurous acid, said acid added in an amount greater than about 15% by weight based on dry weight of lignocellulosic biomass; b) pretreating the lignocellulosic biomass in the pretreatment reactor to provide a pretreated biomass composition, said pretreating conducted at a temperature and for a time selected to produce xylose in an amount that is at least 75% of potentially available xylose; c) subjecting the pretreated biomass composition to a pressure reduction to provide a flash stream and a cooled pretreated biomass composition; d) recovering at least one of sulfur dioxide and sulfurous acid from the flash stream; e) hydrolyzing cellulose from the cooled pretreated biomass composition by enzyme addition to produce glucose; e) fermenting at least a portion of the glucose to ethanol; and f) recycling the at least one of sulfur dioxide and sulfurous acid recovered in d) back into the process.

One aspect of the present disclosure is directed to a process for producing ethanol from lignocellulosic biomass comprising: a) adding acid to lignocellulosic biomass to produce acidified lignocellulosic biomass, said acid comprising at least one of sulfur dioxide and sulfurous acid and said acid added in an amount to provide an equivalent sulfur dioxide loading of at least 15 wt % sulfur dioxide to dry weight lignocellulosic biomass; b) pretreating said acidified lignocellulosic biomass to produce a pretreated biomass composition comprising cellulose, said pretreating conducted in a pressurized pretreatment reactor at a temperature above about 185° C. and for a pretreatment time less than about 10 minutes; c) reducing a pressure of the pretreated biomass composition to produce a flash stream and a cooled pretreated biomass composition; d) obtaining at least one of sulfur dioxide and sulfurous acid from at least one of the flash stream and a stream derived from the flash stream; e) hydrolyzing cellulose from the cooled pretreated biomass composition in the presence of a cellulase to produce glucose; f) fermenting at least a portion of the glucose to ethanol; and g) recycling the at least one of sulfur dioxide and sulfurous acid derived from step d) back into the process.

One aspect of the present disclosure is directed to a process for producing ethanol from lignocellulosic biomass comprising: a) pretreating lignocellulosic biomass in the presence of at least one of sulfur dioxide and sulfurous acid to produce a pretreated biomass composition comprising cellulose, said pretreating conducted in a pressurized pretreatment reactor at a temperature above about 185° C., at a pH less than about 1.5, and at an equivalent sulfur dioxide loading of at least 15 wt % sulfur dioxide to dry weight lignocellulosic biomass; b) reducing a pressure on the pretreated biomass composition to produce a flash stream and a cooled pretreated biomass composition; c) recovering at least one of sulfur dioxide and sulfurous acid from at least one of the flash stream and a stream derived from the flash stream; d) hydrolyzing cellulose from the cooled pretreated biomass composition in the presence of a cellulase to produce glucose; e) fermenting at least a portion of the glucose to ethanol; and g) recycling the at least one of sulfur dioxide and sulfurous acid derived from step c) back into the process.

DETAILED DESCRIPTION

Figure 1:
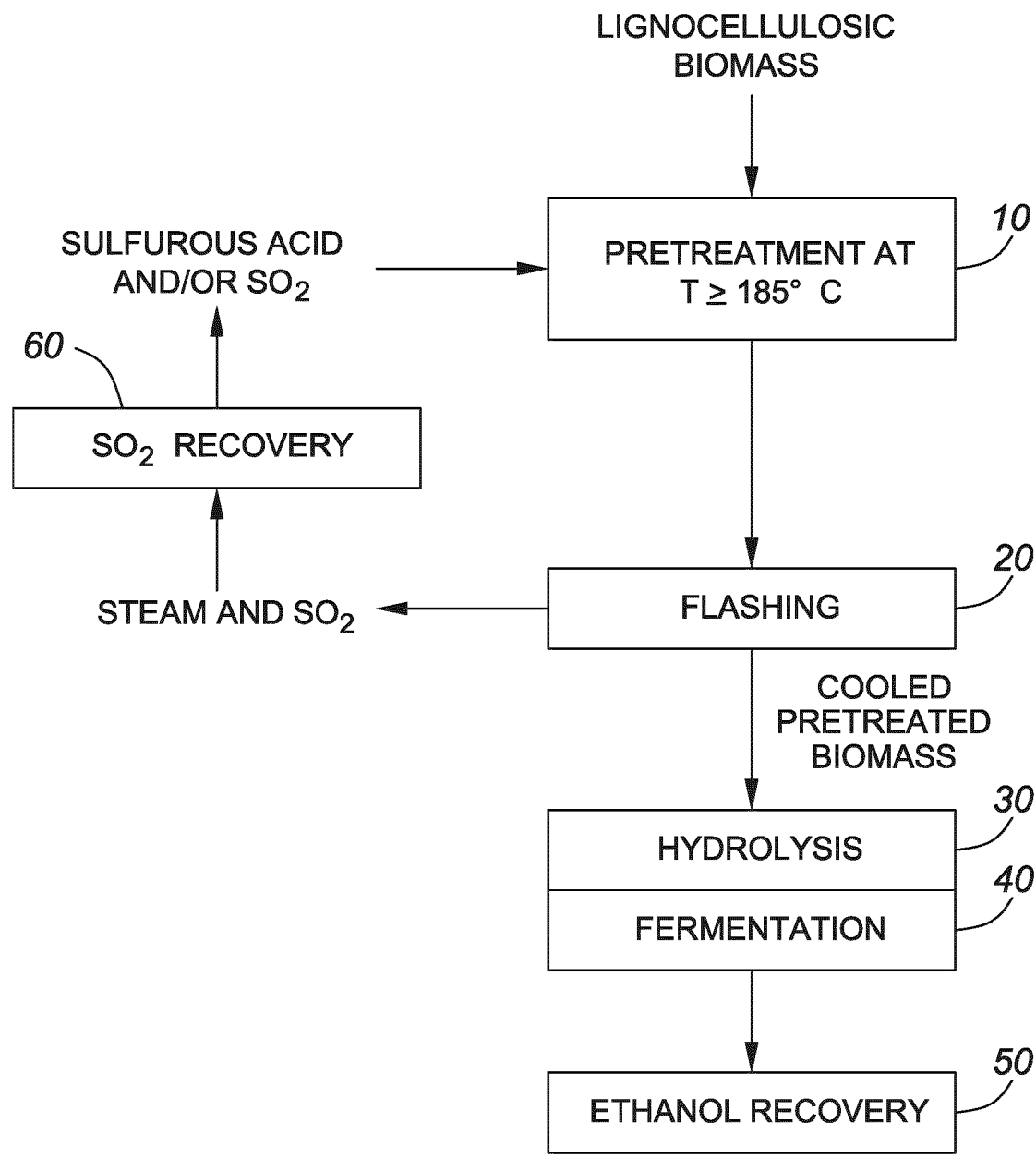
FIG. 1 is a block flow diagram of a method according to one embodiment of the invention.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. The terms "first", "second", etc., may be used to distinguish one element from another, and these elements should not be limited by these terms. Unless defined otherwise, all technical and scientific terms used herein have the same meanings as commonly understood by one of ordinary skill in the art.

Referring to FIG. 1, there is shown a method in accordance with one embodiment of the invention. Lignocellulosic biomass is fed to a pretreatment 10, which involves a heating step, to produce pretreated biomass. The pretreatment 10, which is conducted in a pressurized pretreatment reactor at a temperature above about 185° C., is an acid-catalyzed pretreatment. The acid, which may be added in the pretreatment reactor and/or upstream of the pretreatment reactor, comprises at least one of sulfur dioxide and sulfurous acid. In general, the acid will be added in an amount that results in a pH below about 1.5 and/or that corresponds to a sulfur dioxide loading greater than about 10% weight of sulfur dioxide on dry weight of lignocellulosic biomass, or a loading greater than about 15% weight of sulfur dioxide on dry weight of lignocellulosic biomass. Once the acidified lignocellulosic biomass is heated to the pretreatment temperature and has been in the pretreatment reactor for the residence time, the pressure in the pretreatment reactor is reduced 20 such that a volatile portion of the pretreated biomass composition flashes off in a flash stream comprising steam and sulfur dioxide, while the condensate portion is cooled. The cooled pretreated biomass composition (e.g., the condensate portion) is fed to hydrolysis 30 followed by fermentation 40, or is fed to a combined hydrolysis/fermentation 30/40. The hydrolysis 30 converts cellulose in the cooled pretreated biomass to glucose, while the fermentation converts at least a portion of the glucose to ethanol, which is recovered in an ethanol recovery step 50. The flash stream produced upon flashing 20, which includes both steam and sulfur dioxide, is fed to a sulfur dioxide recovery 60. The sulfur recovery 60 provides sulfur dioxide and/or sulfurous acid in a form suitable for recycling back into the process.

Lignocellulosic Biomass

Lignocellulosic biomass refers to any type of biomass containing cellulose, hemicellulose, and lignin. In general, the combined content of cellulose, hemicellulose and lignin may be greater than 25 wt %. In one embodiment, sucrose, fructose, and/or starch are also present, but in lesser amounts than cellulose and hemicellulose.

In general, the lignocellulosic biomass fed to the pretreatment 10 may include and/or be derived from any lignocellulosic feedstock that needs to be pretreated in order to improve accessibility and/or susceptibility of the lignocellulosic biomass to enzymatic hydrolysis.

Some examples of lignocellulosic feedstock include: (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum (including sweet sorghum), cord grass, rye grass, miscanthus, reed canary grass, C3 grasses such as *Arundo donax* or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover, or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber and corn cobs.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or fines.

Municipal waste includes post-consumer material or waste from a variety of sources such as domestic, commercial, institutional and/or industrial sources. For example, the term includes refuse from waste collection and/or sewage sludge.

Lignocellulosic feedstock can be a mixture of fibers that originate from different kinds of plant materials, including mixtures of cellulosic and non-cellulosic feedstocks.

In one embodiment, the lignocellulosic feedstock is (i) an energy or biomass crop, (ii) an agricultural residue, and/or (iii) hardwood. In one embodiment, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In one embodiment, the lignocellulosic feedstock is a non-woody lignocellulosic feedstock such as (i) an energy crop and/or (ii) an agricultural residue. In one embodiment, the lignocellulosic feedstock is straw, stover, or an energy crop. As used herein, straw refers to the stem, stalk and/or foliage portion of crops remaining after the removal of starch and/or sugar containing components for consumption. Examples of straw include, but are not limited to sugar cane tops and/or leaves, bagasse, oat straw, wheat straw, rye straw, oat straw, rice straw and barley straw. Stover includes the stalk and foliage portion of crops after the removal of starch and/or sugar containing components of plant material for consumption. Examples of stover include, but are not limited to, soybean stover, sorghum stover, and corn stover.

Biomass Preparation

In general, the lignocellulosic biomass may be treated in one or more optional preparatory steps prior to pretreatment 10 and/or as part of the pretreatment 10. Some examples of biomass preparation include size reduction, washing, slurry formation, soaking, dewatering, plug formation, addition of heat, and addition of chemicals (e.g., pretreatment and/or other). In general, these preparatory treatments may depend on the type of biomass and/or selected pretreatment.

In one embodiment, the lignocellulosic biomass is subjected to a size reduction. Some examples of size reduction methods include milling, grinding, agitation, shredding, compression/expansion, and/or other types of mechanical action. Size reduction by mechanical action may be performed by any type of equipment adapted for the purpose, for example, but not limited to, hammer mills, tub-grinders, roll presses, refiners and hydrapulpers. In one embodiment, lignocellulosic feedstock having an average particle size that is greater than about 6-8 inches is subject to a size reduction wherein at least 90% by volume of the particles produced from the size reduction have a length between about 1/16 inch and about 6 inches. Some examples of suitable size reductions and/or equipment are described in WO 2006/026863.

In one embodiment, the lignocellulosic biomass is washed and/or leached with water or an aqueous solution. Washing, which may be performed before, during, or after size reduction, may remove sand, grit, fine particles of the lignocellulosic feedstock, and/or other foreign particles that otherwise may cause damage to the downstream equipment. Leaching, wherein the biomass is in contact with the liquid for more than about 2 minutes, may also remove salts and/or buffering agents. For example, the lignocellulosic biomass may be leached as set forth in WO 02/070753 to Griffin, which is incorporated herein by reference. Alternatively, or additionally, sand may be using other wet or dry sand removal techniques that are known in the art (e.g., including the use of a hydrocyclone or a sieve).

In one embodiment, the biomass is slurried in liquid (e.g., water), which allows the biomass to be pumped. In one embodiment, the biomass is slurried subsequent to size reduction, washing, and/or leaching. The desired weight ratio of water to dry biomass solids in the slurry may be determined by factors such as pumpability, pipe-line requirements, and other practical considerations. For example, in one embodiment, the biomass is slurried to provide a consistency between about 1 wt % and about 40 wt %, or about 1 wt % and about 20 wt %, or between about 4 wt % and about 10 wt %.

In one embodiment, the biomass is soaked in water and/or an aqueous solution (e.g., comprising a pretreatment chemical). In one embodiment, the biomass is soaked subsequent to being slurried (e.g., the slurried biomass is fed to a soaking tank). Feeding the slurried biomass to a soaking tank may allow pretreatment chemical(s) to more uniformly impregnate the biomass, which in turn may provide even cooking in the heating step of pretreatment. For example, soaking the feedstock in a solution comprising a pretreatment chemical (e.g., such as sulfuric acid and/or sulfurous acid) typically provides uniform impregnation of the biomass with the pretreatment chemical. Soaking the feedstock in water, may allow gaseous pretreatment chemicals (e.g., comprising sulfur dioxide) to more uniformly and/or completely impregnate the biomass during subsequent chemical addition steps. In general, uniform impregnation may ensure that some material is not overcooked and/or degraded due to high localized concentration of the pretreatment chemical, and/or that some material is not undercooked (e.g., which may result in low xylose yield and incomplete cellulose hydrolysis). Undercooking or overcooking of lignocellulosic feedstock may be particularly problematic when the heating step of pretreatment is conducted under medium or high solids consistency since the non-uniformity in the concentration of the pretreatment chemical and the temperature are more pronounced.

Soaking is typically conducted in a tank and/or other suitable equipment for handling soaked material. In one embodiment, soaking is conducted at a relatively low consistency (e.g., between about 1 wt % and about 20 wt %, or about 2 wt % and about 18 wt %, or between about 3 wt % and about 15 wt %). In general, soaking may be carried out at any suitable temperature and/or for any suitable duration. For example, in one embodiment, soaking is conducted at a temperature between about 20° C. and about 80° C. and/or for a duration in the range between about 1 minute and about 20 minutes, or longer. In one embodiment, the water or aqueous solution is provided from a recycle stream obtained from other stages of the process. In one embodiment, soaking is conducted in one or more batch or continuous vessels, or a combination thereof, each of which may be a mixed vessel or an unmixed vessel.

In one embodiment, the lignocellulosic biomass is at least partially dewatered to increase the undissolved solids content relative to the incoming biomass. For example, in one embodiment, the lignocellulosic feedstock is at least partially dewatered to provide a predetermined consistency. In general, the term consistency refers the amount of undissolved dry solids or "UDS" in a sample, and is often expressed as a ratio on a weight basis (wt:wt), or as a percent on a weight basis, for example, % (w/w), also denoted herein as wt %. For example, consistency may be determined by filtering and washing the sample to remove dissolved solids and then drying the sample at a temperature and for a period of time that is sufficient to remove water from the sample, but does not result in thermal degradation of the sample. After water removal, or drying, the dry solids are weighed and the weight of water in the sample is the difference between the weight of the sample and the weight of the dry solids. Providing lignocellulosic biomass with a higher consistency to pretreatment may advantageously reduce heating requirements (e.g., since there is less liquid to heat).

In one embodiment, the lignocellulosic biomass is at least partially dewatered in order to remove at least some of the liquid introduced during washing, leaching, slurrying, and/or soaking. In one embodiment, wherein the biomass is subject to dewatering after being slurried and/or after soaking, the water expressed from the biomass in dewatering is recycled back to the slurrying and/or soaking steps.

In one embodiment, dewatering is achieved using a drainer, filtration device, screen, screw press, extruder, or a combination thereof. In one embodiment, dewatering is achieved using a centrifuge. In one embodiment, the dewatering is achieved prior to and/or as part of plug formation. Without being limiting, a plug formation device incorporating a dewatering section may be a pressurized screw press or a plug screw feeder, as described in WO 2010/022511, which is incorporated herein by reference. In one embodiment, the dewatering includes removing water from the biomass under pressure or at atmospheric pressure. In one embodiment, wherein the biomass is subjected to dewatering under pressure, the pressure increase may be caused by one or more high pressure pumps. The pump, or other feeding device, may increase the pressure of the biomass prior to dewatering (e.g., from about 50 psig to about 900 psig, or about 70 psig to about 800 psig or about 140 psig to about 700 psig). The pressure may be measured with a pressure sensor located at a biomass inlet port on a dewatering device or a plug formation device that also dewaters the feedstock. Alternatively, the feedstock subjected to dewatering may be at atmospheric pressure, or at a pressure below about 50 psig.

In one embodiment, the biomass (e.g., which may or may not have been subject to a previous dewatering) is subject to plug formation. In general, plug formation may be considered an integration of lignocellulosic biomass particles into a compacted mass referred to herein as a plug. Plug formation devices may or may not form a plug that acts as a seal between areas of different pressure. In one embodiment, a plug formation device is provided at the front end of the pressurized pretreatment reactor. In one embodiment, the biomass is fed to a plug formation device that dewaters the biomass and/or is disposed downstream of a dewatering device. In one embodiment, the plug formation device that dewaters the biomass includes a housing or shell with openings through which water can pass. Some examples of plug formation devices that dewater biomass include a plug screw feeder, a pressurized screw press, a co-axial piston screw feeder, and a modular screw device.

In one embodiment, the dewatered biomass may have a weight ratio of water to undissolved dry solids between about 0.5:1 (67 wt % dry solids) and about 5:1 (17 wt % dry solids), or between about 1:1 (50 wt % dry solids) and about 4:1 (20 wt % dry solids), or between about 1.5:1 (40 wt % dry solids) to about 4:1 (20 wt % dry solids), or between about 1.5:1 (40 wt % dry solids) and about 3.5:1 (22 wt % dry solids).

In one embodiment, the lignocellulosic biomass is subject to a step that adds heat (e.g., applying extraneous heat, a hot liquid, and/or steam) prior to the lignocellulosic biomass entering the pretreatment reactor. In one embodiment, the biomass is heated as part of the soaking step, as part of a leaching step, or as a separate step. In one embodiment, the biomass is subjected to a steam addition step upstream of entering the pretreatment reactor. In another embodiment, the dewatered biomass is preheated prior to being fed to the pretreatment reactor. For example, in one embodiment, the dewatered biomass is fed to a downstream "heating chamber" or "high shear heating chamber" prior to being fed to a pretreatment reactor. For example, the heating chamber, which may be a horizontally-oriented or essentially horizontally-oriented elongate chamber, may include disintegrating elements for disintegrating the plug of biomass into particles and/or may include inlets for direct steam injection (e.g., to preheat the biomass and provide efficient heat transfer) and/or adding pretreatment chemicals. For example, in one embodiment, a pretreatment chemical such as sulfur dioxide may also be added during direct steam injection in the heating chamber. In one embodiment, the biomass is preheated prior to being fed to the pretreatment reactor using a heating chamber as disclosed, for example, in US. Pat. Publication No. 2013/0071903, which is hereby incorporated by reference. In one embodiment, the operating pressure and temperature of the heating chamber corresponds to the pressure and temperature of the downstream pretreatment reactor. In one embodiment, the biomass is resident in the heating chamber for a duration between about 1 seconds and about 120 seconds, or longer.

As described above, each of the washing, leaching, slurrying, soaking, dewatering, and preheating stages are optional and may or may not be included in the process. In general, if the process is a continuous-flow process, it may be advantageous to include steps of slurrying and dewatering prior to pretreatment in order to improve process economics and efficiency. In addition, providing soaking, preheating, and chemical addition steps upstream of pretreating may provide a more uniform and/or efficient pretreatment. In any case, one or more additional steps/devices may also be provided. For example, without being limiting, examples of such devices include mechanical restricting devices, restraining devices, scrapers and conveyors. For example, in one embodiment, a component and/or device is provided downstream and/or as part of the plug formation device that breaks the plug into segments as it is discharged from the plug formation device, or into other devices positioned downstream of the plug formation device (e.g., into a heating chamber).

Pretreatment

In general, pretreatment refers to one or more steps wherein the lignocellulosic biomass is treated such that the fiber structure thereof is disrupted in order to make the cellulose in the lignocellulosic biomass more susceptible and/or accessible to enzymes in a subsequent hydrolysis.

In one embodiment, pretreatment 10 includes feeding the lignocellulosic biomass into a pretreatment reactor and heating the biomass therein (e.g., directly or indirectly) under pressure. Accordingly, the pretreatment reactor may include one or more valves for maintaining the pretreatment reactor at a predetermined pressure (e.g., greater than about 90 psia and less than about 680 psia) and/or heating means for heating the biomass (e.g., a heating jacket and/or inlets for direct steam injection). Notably, direct steam injection may be advantageous in terms of quickly and uniformly heating high consistency biomass and/or for breaking down the biomass structure via steam explosion.

In one embodiment, the pretreatment 10 includes heating the biomass to a predetermined temperature or temperature range. In general, the predetermined temperature will be greater than about 180° C. For example, in one embodiment, the pretreatment temperature is between about 185° C. and about 300° C., between about 185° C. and about 280° C., and/or between about 185° C. and about 240° C. In one embodiment, the pretreatment temperature is above about 190° C. In practice, there may be a time delay between the time at which the heating process is started and the time when the biomass reaches the predetermined pretreatment temperature.

In general, the pretreatment 10 includes heating the biomass in the pretreatment reactor under acidic conditions. In one embodiment, the acidic conditions are achieved by adding at least one of sulfur dioxide and sulfurous acid to the lignocellulosic biomass. The acid (i.e., comprising sulfur dioxide and/or sulfurous acid) may be added to the lignocellulosic biomass during a soaking step, prior to or after dewatering, prior to or after plug formation, into a heating chamber, into the plug formation device, into the pretreatment reactor, or any combination thereof. For example, in one embodiment, the lignocellulosic biomass is soaked in aqueous sulfurous acid solution, whereas in another embodiment, the lignocellulosic biomass is soaked in water and sulfur dioxide is added to the soaked and at least partially dewatered lignocellulosic biomass in the heating chamber and/or pretreatment reactor. In general, the lignocellulosic biomass and the acid may be added to the pretreatment reactor separately or together. For example, in one embodiment, the acid and steam are added to lignocellulosic biomass fed to the pretreatment reactor. In one embodiment, the acid comprises sulfuric acid in addition to sulfur dioxide and/or sulfurous acid.

The addition of acid (e.g., sulfur dioxide and/or sulfurous acid) to the lignocellulosic biomass, at one or more than one point in the process, provides an acidified lignocellulosic biomass. The term "acidified lignocellulosic biomass" refers to the fact that the pH of a sample of the lignocellulosic biomass corresponds to acidic conditions, and is not intended to indicate whether or not a reaction between the acid and the lignocellulosic biomass occurs.

In general, the acidified lignocellulosic biomass will reside within a reactor zone of the pretreatment reactor for a time referred to as the residence time or pretreatment time. Notably, the residence time does not typically include the time required to ramp the temperature of the lignocellulosic biomass up to the pretreatment temperature. The time that the biomass is held at the pretreatment temperature may be dependent on the type of feedstock, the amount of pretreatment chemicals, and/or the desired degree of pretreatment. In one embodiment, the degree of pretreatment is selected to convert most of the hemicellulose component to soluble sugars (e.g., xylose, mannose, arabinose, and glucose), but little of the cellulose component to sugars (e.g., which may be hydrolyzed in a subsequent enzymatic hydrolysis). For example, in one embodiment, the degree of pretreatment is selected such that the amount of xylan hydrolyzed to xylose is greater than about 50 wt %, about 60 wt %, about 70 wt %, about 80 wt %, or about 90 wt %. In one embodiment, the level of pretreatment is selected to minimize sugar degradation products such as furfural and 5-hydroxymethyl furfural (HFM), which are potential enzymatic hydrolysis inhibitors. In one embodiment, the residence time will be less than about 60 minutes. In one embodiment, the residence time will be less than about 30 minutes. In one embodiment, the residence time will be less than about 10 minutes. In one embodiment, the residence time will be less than 7 minutes. In general, providing a residence time that is greater than about 2 minutes and less than about 10 minutes, when the temperature is greater than about 185° C. may be advantageous in terms of providing an efficient pretreatment without the production of a large number of potentially inhibitory sugar degradation products.

In one embodiment, sufficient acid is added to provide a pH less than 1.5. In another embodiment, sufficient acid is added to provide a pH less than 1.25. In another embodiment, sufficient acid is added to provide a pH close to about 1. The pH of the biomass is measured after all of the acid has been added (e.g., prior to entering the pretreatment reactor, in the pretreatment reactor, or immediately after being discharged from the pretreatment reactor, depending if the acid is added prior to and/or while in the pretreatment reactor). The pH is measured at ambient temperature. In embodiments wherein the acidified and/or pretreated biomass has a large undissolved solids content and/or is relatively thick, the pH will be typically measured from a filtrate, pressate, or centrate (e.g., or other liquid from a solids-liquid separation). For example, in one embodiment, wherein the lignocellulosic feedstock is soaked in sulfurous acid, the pH may be determined from a filtrate of the soaked lignocellulosic feedstock. In another embodiment, wherein all of the acid is added prior to a dewatering step, the pH is measured from the pressate of a pressurized screw press. In another embodiment, wherein at least a portion of the acid is added in a heating chamber or in the pretreatment reactor, a sample of pretreated biomass (e.g., after flashing) is cooled and squeezed to express the liquid, from which the pH is measured. In another embodiment, a sample of pretreated biomass (e.g., after flashing) is centrifuged to provide liquid from which the pH is measured. Although the pH of the pretreatment is generally related to the sulfur dioxide and/or sulfurous acid loading, it may also depend on other factors, including the type of feedstock. For example, if the feedstock has a high alkali content (e.g., potassium) that is not leached and/or washed away, a relatively high sulfur dioxide loading may be required to reach the desired pH.

In one embodiment, sufficient acid is added to provide a sulfur dioxide loading and/or equivalent sulfur dioxide loading of at least 10 wt % (e.g., weight of sulfur dioxide on weight of dry lignocellulosic biomass). In one embodiment, sufficient acid is added to provide a sulfur dioxide loading and/or equivalent sulfur dioxide loading in an amount of at least 15 wt % (e.g., weight of sulfur dioxide on weight of dry lignocellulosic biomass). In one embodiment, sufficient acid is added to provide a sulfur dioxide loading and/or equivalent sulfur dioxide loading in an amount of at least 20 wt % (e.g., weight of sulfur dioxide on weight of dry lignocellulosic biomass). The phrase "sulfur dioxide loading" is used to describe the amount of sulfur dioxide provided, as calculated from the grams of sulfur dioxide provided per gram of dry lignocellulosic biomass as a percentage (e.g., wt %). The term "equivalent sulfur dioxide loading" is used to describe the theoretical amount of sulfur dioxide provided, calculated from the grams of sulfur dioxide or sulfurous acid expressed as equivalent sulfur dioxide provided per gram of dry lignocellulosic biomass.

In one embodiment, the pretreatment conditions (e.g., temperature, pH, sulfur dioxide loading, and/or residence time) are selected to maximize the hydrolysis of xylan and to minimize the hydrolysis of cellulose to glucose. For example, in one embodiment, the pretreatment conditions are selected to provide a relatively low pH (e.g., under 1.5) and a relatively high temperature (e.g., above 180° C., and more specifically above 185°).

In general, any pretreatment reactor that provides the conditions for pretreatment may be used. In one embodiment, the pretreatment reactor is a vertical reactor, a horizontal reactor, or an inclined reactor. In one embodiment, the pretreatment reactor is a vertical reactor and includes a rotary sweeper (not shown) that conveys the heated biomass to a screw conveyor so that it can be discharged via a blow-out valve. In one embodiment, the pretreatment reactor is a horizontal reactor that includes a screw conveyor that leads the heated biomass to the blow-out valve. In one embodiment, the pretreatment reactor is a horizontal reactor and the biomass to be treated therein has a consistency between about 17 wt % and about 67 wt %. In one embodiment, the pretreatment reactor is a horizontal reactor and the biomass to be treated therein has a consistency between about 20 wt % and about 35 wt %.

In embodiments wherein biomass having a consistency between about 17 wt % and about 67 wt % is fed to the pretreatment reactor, and wherein the pretreatment 10 does not significantly break down the cellulose component of the biomass (e.g., although some or all of the hemicellulose component may be hydrolyzed), the biomass discharged from the pretreatment reactor may have a relatively high consistency (e.g., greater than about 15 wt % or even greater than about 20 wt %) and may be relatively hot (e.g., at a temperature greater than about 180° C. and more commonly greater than about 185° C. prior to any flashing).

In one embodiment, the pretreatment reactor is a horizontal reactor. The use of a horizontal reactor may allow a reasonable vapour space to be provided above and/or around a large portion of the biomass. In general, the term vapour space refers to the headspace above the liquid surface, or in the case of a high consistency biomass, above the solids, in the reactor, in addition to the airspace and/or void space in and/or around the wet lignocellulosic biomass. Since the vapour space may contain excess sulfur dioxide that may drive the pretreatment forward and/or may provide a more efficient pretreatment, and since the horizontal configuration allows more lignocellulosic biomass to be adjacent to and/or closer to the vapour space, a more rapid, complete, uniform and/or efficient pretreatment is achieved. For example, the horizontal pretreatment reactor may provide better mass transfer. In one embodiment, the horizontal pretreatment reactor includes an elongated chamber including a screw conveyor. Optionally, the horizontal pretreatment reactor includes a plurality of inlets for injecting steam, sulfur dioxide, and or sulfurous acid, into the elongated heating chamber. In addition to improving efficiency, providing a relatively large headspace volume may also be advantageous for maintaining the pH of the lignocellulosic biomass within a predetermined range during the pretreatment and/or otherwise maintaining a constant amount of acid near the lignocellulosic biomass. For example, if the acid is consumed as the pretreatment progresses, the vapour space, which contains excess sulfur dioxide, may function as a sulfur dioxide and/or sulfurous acid reserve to help drive the reaction and/or prevent localized depletion of the acid. Notably, the use of a horizontal pretreatment reactor is particularly advantageous when the lignocellulosic biomass has a relatively high consistency at the inlet to the pretreatment reactor (e.g., a consistency greater than about 10 wt %), since a relatively large vapour space may allow the vapour phase sulfur dioxide to impregnate the biomass more uniformly.

In one embodiment, the pretreatment reactor is a horizontal reactor for treating lignocellulosic biomass having a consistency greater than 10 wt %, greater than about 15 wt %, or greater than about 20 wt %. In one embodiment, lignocellulosic biomass having a consistency greater than about 18% is fed into the horizontal pretreatment reactor such that there is no little or no headspace (e.g., such that there is a relatively small headspace volume). In this embodiment, the use of the horizontal pretreatment reactor is also advantageous in that it substantially prevents and/or minimizes compaction of the lignocellulosic biomass in a vertical direction (e.g. as a result of the lower weight of lignocellulosic biomass per unit area). Accordingly, there may be more vapour space within the lignocellulosic biomass, wherein excess vapour phase sulfur dioxide may reside (e.g., the voids within the lignocellulosic biomass may function as the sulfur dioxide reserve).

In one embodiment, the equivalent sulfur dioxide loading is selected in dependence upon the vapour space volume and/or consistency of the lignocellulosic biomass. Selecting the equivalent sulfur dioxide loading in dependence upon the vapour space volume is advantageous in that the concentration of the sulfur dioxide available in the vapour phase may be sufficiently high to drive the reaction, replenish sulfur dioxide in solution, and/or maintain a low pH. In general, there may be some compromise when selecting headspace volume. For example, a relatively small headspace may concentrate vapour phase sulfur dioxide close to the lignocellulosic biomass, whereas a larger headspace may contain a larger amount of vapour phase sulfur dioxide. In one embodiment, the headspace volume is between about 1% and about 75% the volume of the pretreatment reactor. In another embodiment, the headspace volume is between about 5% and about 20% the volume of the pretreatment reactor. In one embodiment, wherein the headspace is negligible or relatively small, the consistency is selected such that there is a significant amount of vapour space within the lignocellulosic material. For example, in one embodiment, the consistency is greater than about 10% such that the lignocellulosic biomass is loosely packed. In one embodiment, the ratio of volume of vapour space to volume of lignocellulosic biomass is between 1 and 10. In another embodiment, the ratio of volume of vapour space to volume of lignocellulosic biomass is between 1.5 and 8. In another embodiment, the ratio of volume of vapour space to volume of lignocellulosic biomass is between 2 and 6. In one embodiment, a ratio outside of these ranges is provided. Providing a relatively large vapour space volume advantageously allows vapour phase sulfur dioxide to fill the void area, which may then function as localized sulfur dioxide reservoir(s). Notably, the above described vapour space volume is measured at the start of pretreatment, since these values may change as the pretreatment progresses. In one embodiment, the vapour space volume is determined by determining the volume of water required to fill the reactor containing the lignocellulosic biomass. The volume of lignocellulosic biomass is determined by subtracting the vapour space volume from the reactor volume.

Flashing

After the pretreatment time has elapsed, the pretreated lignocellulosic biomass may be discharged from the pretreatment reactor. In general, this may include reducing the pressure on the pretreated lignocellulosic biomass. Alternatively, the pressure may be reduced at a stage further downstream. In one embodiment, the pressure is reduced by flashing 20. For example, in one embodiment, the pressure is reduced using one or more flash tanks in fluid connection with the pretreatment reactor.

In general, when the pressure on a hot, high-pressure, stream is reduced (e.g., by being discharged into a lower pressure tank referred to as a flash tank), the stream temperature drops, which releases heat that evaporates a volatile portion of the stream (i.e., to produce a flash stream). In general, the temperature of the cooled stream is related to the pressure in the flash tank. For example, if the flash tank is at atmospheric pressure, the stream may be cooled to about 100° C.

In one embodiment, the pretreated lignocellulosic biomass is discharged from the pretreatment reactor into a flash tank that provides a flash stream including steam and sulfur dioxide and a condensate stream comprising a cooled pretreated lignocellulosic biomass composition. For example, the cooled pretreated lignocellulosic biomass composition may comprise undissolved solids such as unconverted cellulose and/or insoluble lignin, and/or soluble compounds such as sugars (e.g., xylose, glucose, and arabinose), organic acids (e.g., acetic acid and glucuronic acid), soluble lignin (e.g., including soluble products of reactions between sulfurous acid and lignin, such as sulfonic acids and lignosulfonic acids), soluble sugar degradation products (e.g., furfural, which may be derived from C5 sugars, and hydroxymethylfurfural (HMF), which may be derived from C6 sugars) and/or one or more salts (e.g., sulfite salts). Notably, although acetic acid, furfural, and/or HMF may be potential inhibitors to fermentation, the use of sulfur dioxide and/or sulfurous acid may produce lower concentrations of these potential inhibitors. More specifically, the use of a relatively high loading of sulfur dioxide and a pretreatment temperature above 185° C. has been found to provide a relatively low amount of inhibitors and/or inactivating compounds. In one embodiment, less than about 5% by weight of furfural relative to the weight of feedstock may be produced. For example, in one embodiment, less than 2.5 g/L of furfural is produced. In another embodiment, less than 1.5 g/L of furfural is produced.

In addition, the use of a relatively high loading of sulfur dioxide and a pretreatment temperature above 185° C. has been found to provide a relatively large amount of xylose. In particular, the pretreatment may be conducted at a temperature and for a time selected to produce xylose in an amount that is at least 75% of the potentially available xylose (e.g., on a weight by weight basis). The amount of potentially available xylose is determined by carbohydrate assay. A method for determining the percentage of potentially available xylose is described in Example 10.

In general, the pretreated biomass composition may be fed to enzymatic hydrolysis 30 with washing, with minimal washing, or without washing. While washing may remove potential inhibitors and/or inactivators, thus increasing enzyme efficiency, it may also remove fermentable sugars, thus reducing ethanol yield. Since the combination of high sulfur dioxide loading and a pretreatment temperature above 185° C. may produce lower concentrations of potential inhibitors and/or inactivators, the process described herein may not require washing, dilution, and/or other processing that removes inhibitors in order to provide a high ethanol yield. Accordingly, in one embodiment, the pretreated feedstock composition is fed to an enzymatic hydrolysis with little or no washing or other processing that removes a significant amount of soluble compounds (e.g., such as lime precipitation). For example, in one embodiment the pretreated feedstock composition is fed to enzymatic hydrolysis such that most of the soluble compounds are transferred to enzymatic hydrolysis with most of the undissolved solids. In one embodiment, the concentration of soluble compounds fed to the enzymatic hydrolysis is at least 20% of the concentration of dissolved solids in the pretreated feedstock composition. In one embodiment, the concentration of soluble compounds fed to the enzymatic hydrolysis is at least about 50% of the concentration of soluble compounds in the pretreated feedstock composition. In one embodiment, at least about 55%, at least about 60%, at least about 65%, at least about 70%, at least about 75%, at least about 80%, at least about 85% or at least 90%, on a weight/volume basis, of the soluble compounds in the pretreated feedstock composition are fed to the enzymatic hydrolysis. In one embodiment, the concentration of soluble compounds in a sample is determined by vacuum filtering the sample through glass microfiber filter paper of pore size 1.6 micron, collecting and weighing the filtrate, drying the filtrate overnight at 105° C., and weighing the contents using an analytical balance. The concentration of soluble compounds may then be expressed as the grams of dry contents per gram of filtrate or grams, of dry contents per liter of filtrate if the density of the filtrate is measured.

According to one embodiment, the concentration of xylose in the stream fed to the enzymatic hydrolysis is at least 50% of the concentration of xylose in the pretreated lignocellulosic biomass composition. According to another embodiment, the concentration of xylose in the stream fed to the enzymatic hydrolysis is at least about 60% of the concentration of xylose in the pretreated lignocellulosic biomass composition. According to another embodiment, the concentration of xylose in the stream fed to the enzymatic hydrolysis is at least about 70% of the concentration of xylose in the pretreated lignocellulosic biomass composition. According to another embodiment, the concentration of xylose in the stream fed to the enzymatic hydrolysis is at least 80% of the concentration of xylose in the pretreated lignocellulosic biomass composition. The concentration of xylose may be determined using HPLC (e.g., after neutralization). Providing little or no washing of the pretreated feedstock composition is advantageous in that it requires less process water and provides a simpler process.

Optionally, the pretreated lignocellulosic biomass composition is subjected to a temperature and/or pH adjustment in order to bring the temperature and/or pH of the pretreated composition into a range compatible with enzyme(s) used in the enzymatic hydrolysis 30 and/or microorganisms used in the fermentation 40. For example, depending upon the pH of the pretreated lignocellulosic biomass composition, a base (e.g., calcium hydroxide, potassium hydroxide, sodium hydroxide, ammonia gas, etc.) may be added to substantially neutralize the pretreated biomass composition. The base may be added to the pretreated biomass composition after it is cooled, before cooling, and/or as it is cooled. In general, the addition of base will be upstream and/or simultaneous with enzyme addition. If base is added downstream of enzyme addition, the contact time of the enzyme with the relatively acidic pretreated biomass composition may be minimized to avoid enzyme inactivation.

In general, the pH at which an enzyme is reasonably active depends on the particular enzyme(s) utilized in the cellulose hydrolysis, and may be determined readily by those of skill in the art. For example, many cellulases may have an optimum pH range between about 4 and about 7, and often about 5. In one embodiment, sufficient pH adjusting chemical is added to bring the pH of the pretreated biomass composition to between about 4 and about 8. In another embodiment, sufficient pH adjusting chemical is added to bring the pH of the pretreated biomass composition to between about 4.5 and about 6.

In general, the temperature at which an enzyme is reasonably active depends on the particular enzyme(s) utilized in the cellulose hydrolysis, and may be determined readily by those of skill in the art. For example, conventional cellulases often have an optimum temperature range between about 40° C. and about 60° C., and more commonly around 50° C., whereas thermostable and/thermophilic enzymes may have optimum temperatures that are much higher (e.g., as high as, or greater than 80° C.).

Advantageously, using a relatively high sulfur loading (e.g., greater than 10 wt %, or greater than 15 wt %) and sulfur dioxide recovery from the flash, when at least 30% to 100% of the $SO_2$ in the flash is recovered and/or recycled improves the economics of the process. In embodiment, at least 50% of initial $SO_2$ charged into the system is flashed off following pretreatment. In embodiment, about 40%-80% of initial $SO_2$ charged into the system is flashed off following pretreatment. In embodiment, more than about 65% of initial $SO_2$ charged into the system is flashed off following pretreatment.

Enzymatic Hydrolysis

After cooling and pH adjustment, enzyme(s) may be added to the pretreated biomass composition using known techniques (e.g., upstream and/or in the hydrolysis reactor). In one non-limiting example, enzyme addition is conducted by adding the enzyme(s) to a reservoir, such as a tank, to form an enzyme solution, which is then introduced to the pretreated biomass composition. In a further non-limiting example, the enzyme(s) is introduced to the pretreated feedstock composition via chemical injection quills, which are commercially available. Alternatively, enzyme may be injected into the pretreated feedstock composition through appropriately sized tubing or via a pipe. In general, addition of enzyme results in an enzymatic hydrolysis 30 wherein the cellulose in the pretreated biomass composition is converted to glucose.

In one embodiment, enzyme addition includes the addition of cellulase, which is an enzyme(s) that breaks cellulose chains into glucose. In particular, the term "cellulase" refers to any of several enzymes produced by fungi, bacteria, or protozoans that catalyze cellulolysis. For example, the term cellulase may denote a multi-enzyme mixture comprising exo-cellobiohydrolases (CBH), endoglucanases (EG) and β-glucosidases (βG) that can be produced by a number of plants and microorganisms. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens*. In addition to CBH, EG and βG, there are several accessory enzymes that may aid in the enzymatic digestion of cellulose (see WO 2009/026722 (Scott), which is incorporated herein by reference and Harris et al., 2010, Biochemistry, 49:3305-3316). These include glycoside hydrolase 61 (GH61), swollenin, expansin, lucinen and cellulose-induced protein (Cip). For example, enzymes containing glycoside hydrolase 61 may improve hydrolysis.

In general, the enzyme dose may depend on the activity of the enzyme at the selected pH and temperature, the reaction time, the volume of the reactor, and/or other parameters. It should be appreciated that these parameters may be adjusted as desired by one of skill in the art to achieve optimal conditions. In one embodiment, the cellulase is added at a dosage between about 2 to 20 mg protein per gram cellulose. In one embodiment, the cellulase is added at a dosage between about 2 to 15 mg protein per gram cellulose. In one embodiment, the cellulase is added at a dosage between about 2 to 12 mg protein per gram cellulose. The protein may be quantified using either the bicinchoninic acid (BCA) assay or the Bradford assay.

In one embodiment, the hydrolysis is conducted at or near the temperature and/or pH optimum of the enzyme(s). For example, conventional cellulase may have optimum pH values between about 4.5 and about 5.5 and a temperature optimum between about 40° C. and about 60° C. In one embodiment, the enzymatic hydrolysis is conducted at a temperature above about 56° C., or 57° C. Conducting the hydrolysis at temperatures above about 56° C., and in particular, at temperatures above 57° C. or 58° C. may be advantageous in that microbial contamination may be reduced. Reduced microbial contamination may be particularly advantageous in $SO_2$ catalyzed systems, wherein the production of inhibitors to microbial contamination may be lower.

In one embodiment, the enzymatic hydrolysis and fermentation are conducted in separate vessels so that each biological reaction can occur at its respective optimal temperature. For example, in one embodiment, the hydrolysis is conducted in one or more dedicated hydrolysis reactors, which may be connected in series or in parallel. In general, the hydrolysis may be conducted in continuous, fed-batch, or batch mode. In one embodiment, the hydrolysis is conducted in continuous mode, which may offer greater productivity and lower costs. For example, in one embodiment, the hydrolysis is conducted one or more continuous stirred tank reactors (CSTRs) and/or one or more plug flow reactors (PFRs). In the plug flow reactor, the slurry is pumped through a pipe or tube such that it exhibits a relatively uniform velocity profile across the diameter of the pipe/tube and such that residence time within the reactor provides the desired conversion. In one embodiment, the hydrolysis includes a plurality of hydrolysis rectors including a PFR and a CSTR in series, as for example, described in U.S. Pat. No. 8,709,770, which is hereby incorporated by reference. In general, the number of hydrolysis reactors in the system may depend on the cost of the reactors, the volume of the pretreated biomass composition, and/or other factors. For a commercial-scale ethanol plant, the typical number of hydrolysis reactors may be, for example, 4 to 12. In order to maintain the desired hydrolysis temperature, the hydrolysis reactors may be jacketed with steam, hot water, or other heat sources. The total residence time in the enzymatic hydrolysis reactors is typically between about 24 hours and about 250 hours, depending on the degree of conversion desired, although could be shorter or longer.

Fermentation

In fermentation 40, the sugars produced during pretreatment (e.g., xylose and glucose) and/or enzymatic hydrolysis (e.g., glucose) are converted to alcohols, and in particular, to ethanol. More specifically, the fermentation uses one or more microorganisms to convert the sugars to ethanol.

In general, the fermentation microorganism(s) may include any yeast and/or bacteria. For example, in one embodiment, the fermentation is carried out with *Saccharomyces* spp. yeast, which are attractive because of their capacity to produce ethanol.

In one embodiment, glucose and/or other hexoses derived from the cellulose are fermented to ethanol using a wild-type *Saccharomyces cerevisiae* or a genetically modified yeast. In one embodiment, xylose and or arabinose derived from the hemicelluloses are fermented to ethanol using a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (see for example U.S. Pat. Nos. 5,789,210, 5,866,382, 6,582,944 and 7,527,927 and European Patent No. 450530) or (b) fungal or bacterial xylose isomerase (XI) gene (see for example U.S. Pat. Nos. 6,475,768 and 7,622,284). Examples of yeasts that have been genetically modified to ferment L-arabinose include, but are not limited to, recombinant *Saccharomyces* strains into which genes from either fungal (for example U.S. Pat. No. 7,527,951) or bacterial (for example WO 2008/041840) arabinose metabolic pathways have been inserted. Alternatively, xylose and other pentose sugars may be fermented to xylitol by yeast strains selected from the group consisting of *Candida, Pichia, Pachysolen, Hansenula, Debaryomyces, Kluyveromyces* and *Saccharomyces*.

The dose of the microorganism(s) will depend on other factors, such as the activity of the microorganism, the desired reaction time, the volume of the reactor and other parameters. It should be appreciated that these parameters may be adjusted as desired by one of skill in the art to achieve optimal conditions.

In one embodiment, the fermentation may be performed at or near the temperature and/or pH optimum of the corresponding microorganism. For example, *Saccharomyces cerevisiae* may have optimum pH values between about 4 and about 5.5 and a temperature optimum between about 25° C. and about 35° C.

In one embodiment, the enzymatic hydrolysis and fermentation are conducted in separate vessels so that each biological reaction can occur at its respective optimal temperature. In another embodiment, the hydrolysis (e.g., which may be also referred to as saccharification) is conducted simultaneously with the fermentation in same vessel. For example, in one embodiment, a simultaneous saccharification and fermentation (SSF) is conducted at temperature between about 35 and 38° C., which is a compromise between the 50-55° C. optimum for cellulase and the 25-35° C. optimum for yeast.

Regardless of whether the biological conversion includes a separate hydrolysis and fermentation (SHF), simultaneous saccharification and fermentation (SSF), or hybrid hydrolysis and fermentation (HHF) (e.g., wherein the two separate steps are conducted in a same reactor, but at different temperatures), the reactor(s) may contain the C5 sugars and/or the C6 sugars. More specifically, the reactors may contain not only the glucose released during cellulose hydrolysis, but also one or more sugars arising from the pretreatment (e.g., xylose, glucose, arabinose, mannose, and/or galactose), for a co-fermentation. Alternatively, in a SHF, the C5 sugars and/or C6 sugars produced during pretreatment are fed to a separate fermentation reactor and/or series of reactors than the C6 sugars produced during enzymatic hydrolysis.

In one embodiment, the fermentation is conducted on a sugar solution containing both C5 and C6 sugars using only *Saccharomyces cerevisiae*. In another embodiment, the fermentation is conducted on a sugar solution containing both C5 and C6 sugars using a mixture wherein C5 utilizing and ethanol producing yeasts (e.g., such as *Pichia fermentans* and *Pichia stipitis*) are cocultured with *Saccharomyces cerevisiae*.

In one embodiment, the fermentation is supplemented with additional nutrients required for the growth of the fermentation microorganism. For example, yeast extract, specific amino acids, phosphate, nitrogen sources, salts, trace elements and vitamins may be added to the hydrolyzate slurry to support their growth. In one embodiment, yeast recycle is employed.

In general, the fermentation may be conducted in continuous, fed-batch, or batch mode. In one embodiment, the fermentation is conducted in continuous mode, which may offer greater productivity and lower costs. In one embodiment, the fermentation is conducted in a plurality of fermentation tanks. For example, in one embodiment, the fermentation is conducted one or more continuous stirred tank reactors (CSTRs) and/or one or more plug flow reactors (PFRs). Advantageously, continuous mode operation may offer less reactor down time and smaller reactor volumes.

Ethanol Recovery

In general, the ethanol produced during fermentation is recovered 50, a process wherein ethanol may be concentrated and/or purified from the fermented solution (e.g., which may or may not have been subjected to a solids-liquid separation to remove unconverted cellulose, insoluble lignin, and/or other undissolved substances).

In one embodiment, ethanol recovery uses one or more distillation columns that separate the ethanol from other components (e.g., water). In general, the distillation column(s) in the distillation unit may be operated in continuous or batch mode, although are typically operated in a continuous mode. Heat for the distillation process may be introduced at one or more points, either by direct steam injection or indirectly via heat exchangers. After distillation, the water remaining in the concentrated ethanol stream (i.e., vapour) may be removed from the ethanol rich vapour by a molecular sieve resin, by membrane extraction, or other methods known to those of skill in the art for concentration of ethanol beyond the 95% that is typically achieved by distillation (e.g., a vapour phase drying). The vapour may then be condensed and denatured.

Sulfur Dioxide Recovery

In general, sulfur dioxide obtained from the flash stream may be sent to sulfur dioxide recovery 60. More specifically, the flash stream, which contains excess sulfur dioxide and/or sulfur dioxide generated from solution as a result of the increased temperature and/or pressure reduction, is fed to a sulfur dioxide recovery unit.

In general, gas containing sulfur dioxide having a concentration in the range of about 1% to about 100% may be purified and/or condensed and/or may be used to provide liquid sulfur dioxide. For example, some processes of purifying and/or condensing sulfur dioxide gas and/or preparing liquid sulfur dioxide, which can be used to provide gas phase sulfur dioxide, include compressing and condensing (e.g., at high sulfur dioxide concentrations), partial condensation (e.g., at low sulfur dioxide concentrations), and absorption and acidification (e.g., scrubbing low concentrations of sulfur dioxide with ammonium bisulfite). For example, at atmospheric pressure pure sulfur dioxide will condense at −10.1° C., and at increased pressures will begin to condense at higher temperatures (i.e., will condense at 32.2° C. at 388 kPa (56.3 psig)).

In one embodiment, the sulfur dioxide recovery 60 includes a partial condenser that provides a first stream comprising a condensate (e.g., from the steam) and a second stream comprising gaseous sulfur dioxide. In one embodiment, the first stream comprising the condensate may be fed to a sulfur dioxide stripper, which removes any residual sulfur dioxide from the condensate to provide another stream of gaseous sulfur dioxide (e.g., the two streams of gaseous sulfur dioxide are optionally combined to provide a combined gas stream). The sulfur dioxide gas stream, or combined sulfur dioxide stream, may be dried (e.g., by countercurrent washing with 98% sulfuric acid), compressed, and condensed as liquid sulfur dioxide. In one embodiment, the liquid sulfur dioxide, which is optionally stored temporarily, is recycled directly back into the process. In one embodiment, the recycling includes generating gaseous sulfur dioxide from liquid sulfur dioxide for impregnating the lignocellulosic biomass, or forming a sulfurous acid solution that is used to impregnate the lignocellulosic biomass. In one embodiment, gaseous sulfur dioxide is compressed and stored for recycling back into the process.

In one embodiment, the sulfur dioxide recovery 60 includes a sulfur dioxide scrubbing system. For example, in one embodiment, the sulfur dioxide scrubbing system comprises one or more packed absorbers (e.g., in series). In one embodiment, the absorbers include amine-based, alkali-based, or other absorbers.

In one embodiment, the sulfur dioxide recovery 60 includes a regenerative sulfur dioxide scrubbing system. In one embodiment, the sulfur dioxide-rich absorbers are fed to a regeneration or stripping column in which the sulfur dioxide is removed (e.g., by steam) and the absorber regenerated. In one embodiment, the regenerative sulfur dioxide scrubbing system is wet sulfur dioxide scrubbing system. In one embodiment, the regenerative sulfur dioxide scrubbing system is a dual alkali system using a first alkali absorber to scrub the gas stream, and a second alkali to regenerate the absorber.

In one embodiment, the regenerative sulfur dioxide scrubbing system is disposed downstream of a partial condenser that provides a first stream comprising a condensate (e.g., from the steam) and a second stream comprising gaseous sulfur dioxide. For example, in one embodiment, the second stream comprising gaseous sulfur dioxide is fed to a regenerative wet sulfur dioxide scrubbing system to provide the recovered sulfur dioxide. In one embodiment, the recovered sulfur dioxide is further processed to provide commercial grade liquid sulfur dioxide. In one embodiment, the recovered or further processed sulfur dioxide gas stream is dried (e.g., by countercurrent washing with 98% sulfuric acid), compressed, and condensed as liquid sulfur dioxide. Alternatively, the recovered sulfur dioxide is converted into elemental sulfur, which may be used to provide the recycled sulfur dioxide.

In one embodiment, the sulfur recovery 60 comprises a sulfur burner, which burns sulfur in the presence of a high concentration of oxygen, to provide the sulfur dioxide. In one embodiment, the sulfur recovery 60 comprises a sulfur burner that uses the flash stream, or a stream derived from the flash stream, to reduce the temperature in the sulfur burner.

Advantageously, the sulfur dioxide recovery 60 allows the recycling of sulfur within the system, and thus improves the process economics (e.g., since less sulfur dioxide and/or sulfurous acid needs to be purchased for pretreatment). In addition, the sulfur dioxide recovery improves the economics of using a high sulfur dioxide loading, particularly, when the sulfur dioxide recovery 60 is efficient at high sulfur dioxide concentrations. Accordingly, the process may exploit the advantages of combining high sulfur dioxide loadings with temperatures above about 185° C. (e.g., fewer and/or lower concentrations of potential inhibitors combined with a more efficient pretreatment), without significant increases in cost.

In fact, providing relatively high sulfur dioxide loadings (e.g., either from gaseous sulfur dioxide and/or sulfurous acid) without a volatile solvent (e.g., ethanol) advantageously facilitates a simple flash steam recovery of sulfur dioxide. In addition, it simplifies any further purification and/or processing of the sulfur dioxide recovered from the flash stream. Since the recovery may be relatively simple and efficient, the cost of the relatively high sulfur loading is not as limiting. Accordingly, the advantages of using a high sulfur loading for pretreatment may be exploited. Notably, in addition to the cost of high sulfur dioxide loading, sulfur dioxide may not have been used at high loadings in pretreatment because with the pKa of sulfur dioxide being about 1.81, at pH values above 1.8, the bisulfite species ($HSO_3^-$) may be more predominant. Bisulfite and or bisulfite salts have been considered in sulfite pretreatment to overcome recalcitrance of lignocellulose (SPORL) processes. In fact, although the pH of acid pretreatment has been reported as being less than 5, it is generally understood that when the pH is less than about 2, the pretreatment is conducted with a strong acid such as sulfuric or hydrochloric acid.

Advantageously, the combination of relatively high sulfur dioxide loading and a pretreatment temperature above about 185° C. has been found to produce fewer and/or less inhibitors/inactivators, and/or a concentration of inhibitors/inactivators that does not significantly affect the ethanol yield from fermentation, even when the pretreated lignocellulosic biomass composition is not substantially washed, diluted, and/or otherwise treated to reduce fermentation inhibition/inactivation (e.g., other than the pH and/or temperature adjustment to where the enzyme(s) is reasonably active).

Further advantageously, the combination of a relatively high sulfur dioxide loading and a pretreatment temperature above about 185° C. has been found to dissolve a large portion of the lignin (e.g., at least 50%) and/or to hydrolyze at least 70% of the hemicellulose. For example, when acid is added in an amount equivalent to at least 10 wt % sulfur dioxide per dry weight of lignocellulosic biomass up to 90% of the hemicellulose may be dissolved.

Further advantageously, the combination of a relatively high sulfur dioxide loading and a pretreatment temperature above about 185° C. may reduce the enzyme usage. In particular, it has been found that when acid is added in an amount equivalent to at least 10% weight sulfur dioxide per dry weight of lignocellulosic biomass, the amount of glucose converted in the washed $SO_2$ system is increased relative to the washed $H_2SO_4$ system, and more surprisingly, that the amount of glucose converted in the unwashed $SO_2$ system is markedly increased relative to an unwashed $H_2SO_4$ system (e.g., wherein the washing refers to a washing step between pretreatment and enzymatic hydrolysis). Providing a pretreatment process that provides a relatively high glucose conversion (e.g., or alternatively uses less enzyme) for unwashed systems may be important in terms of commercial success. Utilizing a relatively high equivalent sulfur dioxide loading in a process that provides little or no washing, in combination with sulfur dioxide loading has further advantages. For example, since the sulfur dioxide is flashed off subsequent to pretreatment but prior to enzymatic hydrolysis, and more specifically, prior to pH adjustment for enzymatic hydrolysis, there will be fewer salts formed (e.g., which are potential inhibitors). Moreover, since a high sulfur dioxide loading is used, sulfur dioxide recovery may be relatively simple and/or more cost effective.

Figure 2:
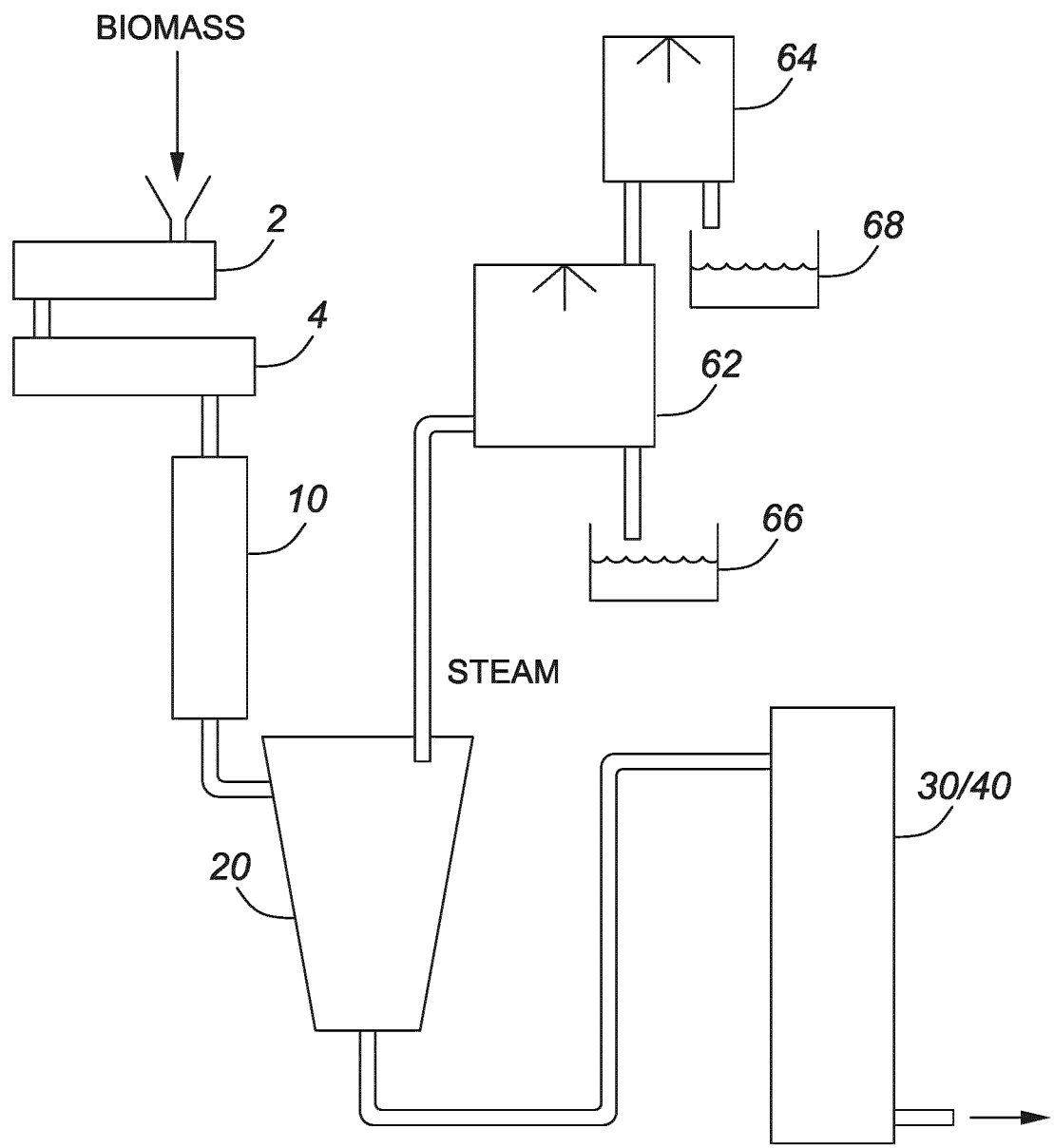
FIG. 2 is a schematic diagram showing a system for producing ethanol in accordance with one embodiment of the invention.

Referring to FIG. 2, there is shown one embodiment of a system including a sulfur dioxide recovery. In operation, lignocellulosic biomass is slurried and provided to a pressurized dewatering system 2, an optional heating chamber 4, and a pretreatment reactor 10. Although illustrated as three separate components for demonstrative purposes, it should be understood that the pretreatment reactor may be part of a pretreatment system that includes these and/or other components, which may be provided as one or more separate components and/or as integrated components. For example, in one embodiment, the pretreatment is provided according to one of the pretreatment systems described in US Publ. Nos. 2010/0056774 and/or 2013/0071903, which are hereby incorporated by reference and particularly for the purpose of describing such pretreatment systems.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2. The pressurized dewatering system may include a predraining zone (not shown), wherein at least some of the water is removed and fed to a high pressure pump (not shown), which creates a high pressure zone for further dewatering. The pressurized dewatering system 2 reduces the moisture content of the biomass to an amount selected for pretreatment. For example, in one embodiment, the pressurized dewatering system 2 includes a pressurized dewatering press or a pressurized plug screw feeder (e.g., as described in US Publ. No. 2010/0056774). In one embodiment, the pressured dewatering system 2 is at a pressure between about 70 psia and about 800 psia. The dewatered biomass (e.g., which may or may not be in plug form and may have a consistency between about 20 wt % and about 67 wt %), may then be fed to the optional heating chamber 4, as for example, described in US Publ. No. 2013/0071903, and then to the pretreatment reactor 10.

Sulfur dioxide and/or sulfurous acid may be added in the pressurized dewatering system 2, in the heating chamber 4, and/or directly into the pretreatment reactor 10. For example, in one embodiment, gaseous sulfur dioxide is added to the biomass upstream of the inlet of a pressurized screw press, at the inlet to a pressurized screw press, in a dewatering zone of a pressurized screw press, in the pressurized plug screw feeder, and/or in the reaction zone of the pretreatment reactor.

The pretreatment reactor 10, which for exemplary purposes is shown as a vertical reactor, may be any reactor that may contain the biomass while the biomass is subject to at least a portion of the pretreatment. For example, in one embodiment the pretreatment reactor is a vertical reactor, such as an upflow or downflow vertical reactor. In another embodiment, the pretreatment reactor is a horizontal or inclined reactor. The pretreatment reactor 10 may be equipped with an internal mechanism, such as a screw, conveyor, or similar mechanism, for conveying the lignocellulosic biomass within a reactor zone of the pretreatment reactor.

In one embodiment, the pretreatment reactor includes one or more inlets for injecting steam into the biomass. Accordingly, the pretreatment reactor may be held at a predetermined temperature and/or pressure. For example, in one embodiment the one or more inlets for injecting steam are provided near the reactor zone of the pretreatment reactor 10.

In general, the biomass will be treated in the pressurized pretreatment reactor 10 at an elevated temperature (e.g., above 185° C.) for a specific amount of time. In general, the temperature, pressure, and/or residence time of the biomass in the reaction zone may depend upon a number of variables, including the pH in the reaction zone and the desired degree of pretreatment. In one embodiment, the biomass has a residence time in the pretreatment reactor from about 10 seconds to about 20 minutes, or about 10 seconds to about 10 minutes. The pH for the pretreatment may be between about 0.5 and about 1.5, or between about 1.0 and about 1.5. Notably, the partially dewatered lignocellulosic feedstock may be heated prior to its entry into the reaction zone (e.g., in the optional heating chamber 4), in the reaction zone, or a combination thereof.

When the biomass has been resident in the reactor zone of the pretreatment reactor 10 for the pretreatment time, the pretreated biomass is then discharged into a flash tank 20 to provide the pretreated biomass. Since the flash tank 20 is held at a pressure that is lower than the pressure of the pretreatment reactor 10, the temperature of the pretreated biomass will drop from the pretreatment temperature to a temperature dependent on the pressure in the flash tank. For example, if the flash tank is at about atmospheric pressure, the pretreated biomass temperature will be about 100° C. If the flash tank is below atmospheric pressure, the temperature will be lower than 100° C. If the flash tank is held above atmospheric pressure, the temperature will be greater than 100° C.

The cooled, pretreated biomass composition produced by the pretreatment 10 and flashing 20 is fed to hydrolysis 30 or a combined hydrolysis/fermentation 30/40, followed by ethanol recovery (not shown). Depending on the temperature and/or pH of the cooled, pretreated biomass composition, it may be subjected to a temperature and/or pH adjustment (not shown). For example, in one embodiment, the cooled, pretreated biomass composition is actively cooled.

The flash stream exiting from the top of the flash tank 20 may include steam, gaseous sulfur dioxide, and/or other volatile compounds (e.g., which depend on the pressure of the flash tank). The flash stream is fed to a two-stage system. More specifically, the flash stream is fed to a partial condenser 62, wherein most of the steam is condensed and collected in reservoir 66. For example, the partial condenser may include a tower that is suitably packed and provided with a water spray or shower. The sulfur dioxide gas passes through the partial condenser and exits from the top, where it is fed to a sulfur dioxide absorption tower 64. The second stage sulfur dioxide absorption tower 64, which is likewise packed with a suitable packing material and equipped with a water spray or shower, provides a cool spray of water that absorbs the sulfur dioxide to form a sulfurous acid solution that is collected in reservoir 68. Notably, while the temperature of the water spray in tower 64 is selected to absorb sulfur dioxide, the temperature of the water in tower 62 is selected to keep the sulfur dioxide in gaseous form (e.g., is higher). Nevertheless, the aqueous solution in reservoir 66 may contain some sulfur dioxide and thus may be fed to a sulfur dioxide stripper for further processing. The sulfurous acid solution from the reservoir 68 may be further purified and/or concentrated and recycled back into the process (i.e., to provide the catalyst for pretreatment).

Figure 3:
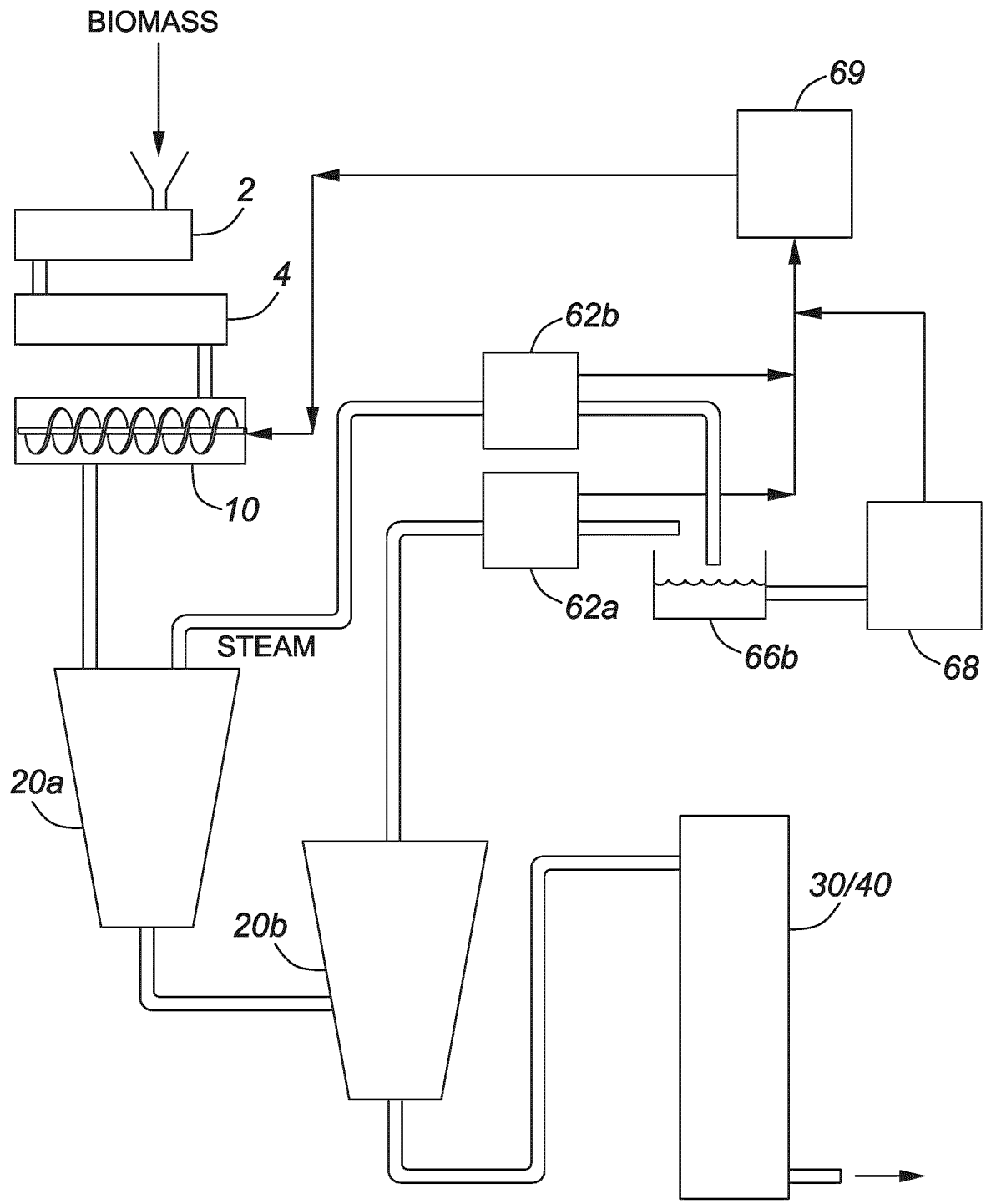
FIG. 3 is a schematic diagram showing a system for producing ethanol in accordance with another embodiment of the invention.

Referring to FIG. 3, there is shown another embodiment of a system including a sulfur dioxide recovery. In operation, lignocellulosic biomass is slurried and provided to a pressurized dewatering system 2, an optional heating chamber 4, and a pretreatment reactor 10. Although illustrated as three separate components for demonstrative purposes, it should be understood that the pretreatment reactor may be part of a pretreatment system that includes these and/or other components, which may be provided as one or more separate components and/or as integrated components. For example, in one embodiment, the pretreatment is provided according to one of the pretreatment systems described in US Publ. Nos. 2010/0056774 and/or 2013/0071903, which are hereby incorporated by reference and particularly for the purpose of describing such pretreatment systems.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2. The pressurized dewatering system may include a predraining zone (not shown), wherein at least some of the water is removed and fed to a high pressure pump (not shown), which creates a high pressure zone for further dewatering. The pressurized dewatering system 2 reduces the moisture content of the biomass to an amount suitable for pretreatment. For example, in one embodiment, the pressurized dewatering system 2 includes a pressurized dewatering press or a pressurized plug screw feeder (e.g., as described in US Publ. No. 2010/0056774). In one embodiment, the pressured dewatering system 2 is at a pressure between about 70 psia and about 800 psia. The dewatered biomass (e.g., which may or may not be in plug form and may have a consistency between about 20 wt % and about 67 wt %), may then be fed to the optional heating chamber 4, as for example, described in US Publ. No. 2013/0071903, and then to the pretreatment reactor 10.

Sulfur dioxide and/or sulfurous acid may be added in the pressurized dewatering system 2, in the heating chamber 4, and/or directly into the pretreatment reactor 10. For example, in one embodiment, gaseous sulfur dioxide is added to the biomass upstream of the inlet of a pressurized screw press, at the inlet to a pressurized screw press, in a dewatering zone of a pressurized screw press, in the pressurized plug screw feeder, and/or in the reaction zone of the pretreatment reactor.

The pretreatment reactor 10, which for exemplary purposes is shown as a horizontal reactor, may be any reactor that may contain the biomass while the biomass is subject to at least a portion of the pretreatment. The pretreatment reactor 10 may be equipped with an internal mechanism, such as a screw, conveyor, or similar mechanism, for conveying the lignocellulosic feedstock within a reactor zone of the pretreatment reactor.

In one embodiment, the pretreatment reactor includes one or more inlets for injecting steam into the biomass. Accordingly, the pretreatment reactor may be held at a predetermined temperature and/or pressure. For example, in one embodiment the one or more inlets for injecting steam are provided near the reactor zone of the pretreatment reactor 10.

In general, the biomass will be treated in the pressurized pretreatment reactor 10 at an elevated temperature (e.g., above 185° C.) for a specific amount of time. In general, the temperature, pressure, and/or residence time of the biomass in the reaction zone may depend upon a number of variables, including the pH in the reaction zone and the degree of pretreatment. In one embodiment, the biomass has a residence time in the pretreatment reactor from about 10 seconds to about 20 minutes, or about 10 seconds to about 600 seconds. The pH for the pretreatment may be between about 0.5 and about 1.5, or between about 1.0 and about 1.5. Notably, the partially dewatered lignocellulosic feedstock may be heated prior to its entry into the reaction zone (e.g., in the optional heating chamber 4), in the reaction zone, or a combination thereof.

When the biomass has been resident in the reactor zone of the pretreatment reactor 10 for the pretreatment time, the pretreated biomass is then discharged into a flash tank 20a to provide the pretreated biomass. Since the flash tank 20a is held at a pressure that is lower than the pressure of the pretreatment reactor 10, the temperature of the pretreated biomass will drop from the pretreatment temperature to a temperature dependent on the pressure in the flash tank 20a. In this embodiment, the first flash tank 20a and a second flash tank 20b are part of a flashing system. In general, the pressure of the first flash tank 20a will be higher than the pressure of the second flash tank 20b. Since the first flash tank 20a is held at a pressure that is lower than the pressure of the pretreatment reactor 10, but higher than the pressure of the second flash tank 20b, the temperature of the pretreated biomass composition will drop as it passes from the pretreatment reactor 10, to the first flash tank 20a, and to the second flash tank 20b.

The cooled, pretreated biomass composition produced by the pretreatment 10 and flashing 20 (e.g., 20a/20b) is fed to hydrolysis 30 or a combined hydrolysis/fermentation 30/40, followed by ethanol recovery (not shown). Depending on the temperature and/or pH of the cooled, pretreated biomass composition, it may be subjected to a temperature and/or pH adjustment (not shown). For example, in one embodiment, the cooled, pretreated biomass composition is actively cooled.

The flash stream vented from each of the flash tanks 20a/20b is fed to partial condensers 62a/62b, respectively, wherein most of the steam therein is condensed to provide a condensate that is collected at 66b. The condensate from 66b, which may contain a relatively small amount of sulfur dioxide, is fed to an open-steam stripping column 68, which provides stream of gaseous sulfur dioxide. The sulfur dioxide gas from the tops of columns 62a, 62b, and 68 is compressed and condensed and temporarily stored 69 as liquid sulfur dioxide for eventual recycle back into the process.

Figure 4:
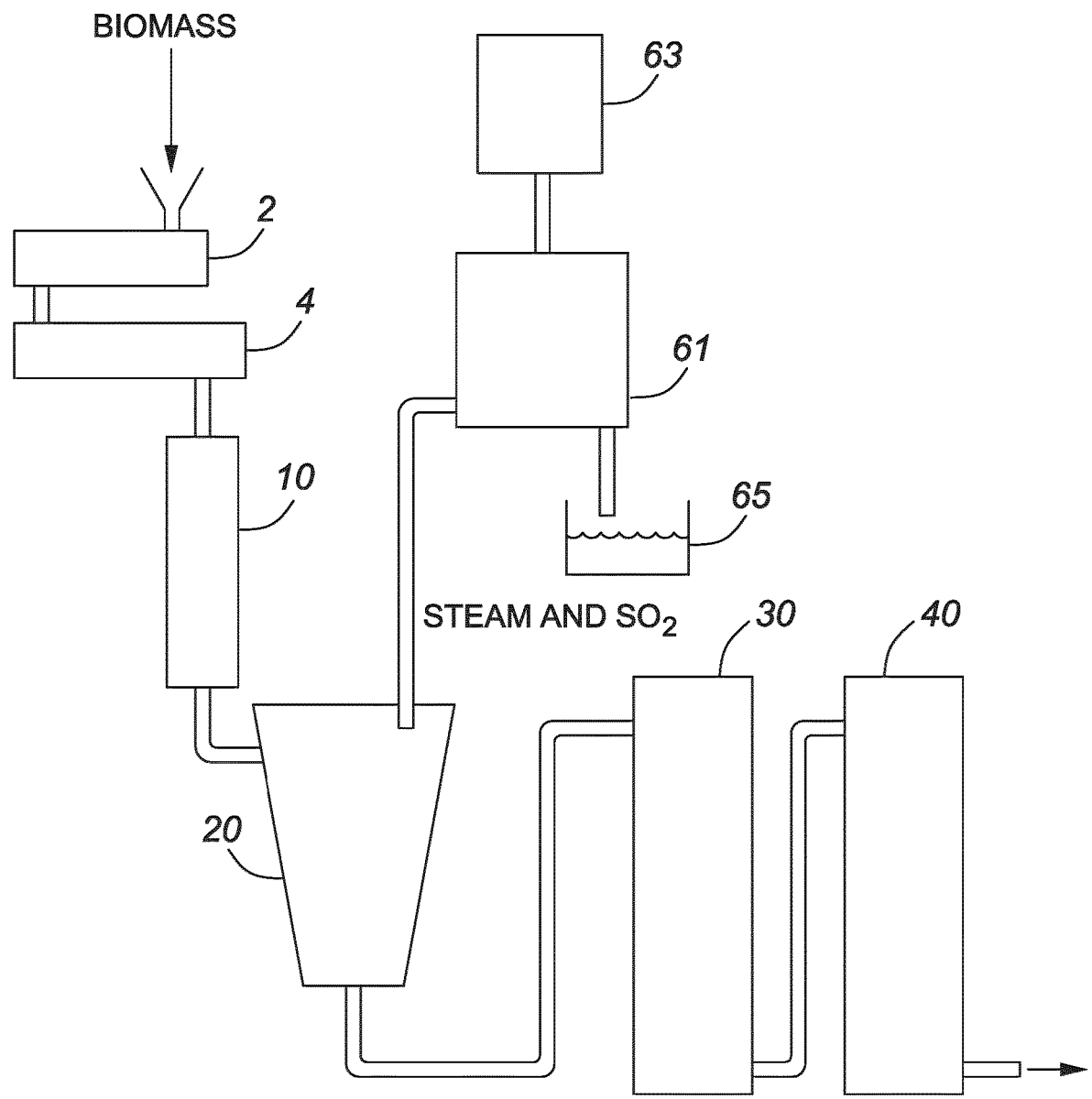
FIG. 4 is a schematic diagram showing a system for producing ethanol in accordance with another embodiment of the invention.

Referring to FIG. 4, there is shown one embodiment of a system including a sulfur dioxide recovery. In operation, lignocellulosic biomass is slurried and provided to a pressurized dewatering system 2, an optional heating chamber 4, and a pretreatment reactor 10. Although illustrated as three separate components for demonstrative purposes, it should be understood that the pretreatment reactor may be part of a pretreatment system that includes these and/or other components, which may be provided as one or more separate components and/or as integrated components.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2. The pressurized dewatering system may include a predraining zone (not shown), wherein at least some of the water is removed and fed to a high pressure pump (not shown), which creates a high pressure zone for further dewatering. The pressurized dewatering system 2 reduces the moisture content of the biomass to an amount suitable for pretreatment. For example, in one embodiment, the pressurized dewatering system 2 includes a pressurized dewatering press or a pressurized plug screw feeder (e.g., as described in US Publ. No. 2010/0056774). In one embodiment, the pressured dewatering system 2 is at a pressure between about 70 psia and about 800 psia. The dewatered biomass (e.g., which may or may not be in plug form and may have a consistency between about 20 wt % and about 67 wt %), may then be fed to the optional heating chamber 4, as for example, described in US Publ. No. 2013/0071903, and then to the pretreatment reactor 10.

Sulfur dioxide and/or sulfurous acid may be added in the pressurized dewatering system 2, in the optional heating chamber 4, and/or directly into the pretreatment reactor 10. For example, in one embodiment, gaseous sulfur dioxide is added to the biomass upstream of the inlet of a pressurized screw press, at the inlet to a pressurized screw press, in a dewatering zone of a pressurized screw press, in the pressurized plug screw feeder, and/or in the reaction zone of the pretreatment reactor.

The pretreatment reactor 10, which for exemplary purposes is shown as a vertical reactor, may be any reactor that may contain the biomass while the biomass is subject to at least a portion of the pretreatment. For example, in one embodiment, the pretreatment reactor is a horizontal or inclined reactor. The pretreatment reactor 10 may be equipped with an internal mechanism, such as a screw, conveyor, or similar mechanism, for conveying the lignocellulosic biomass within a reactor zone of the pretreatment reactor.

In one embodiment, the pretreatment reactor includes one or more inlets for injecting steam into the biomass. Accordingly, the pretreatment reactor may be held at a predetermined temperature and/or pressure. For example, in one embodiment the one or more inlets for injecting steam are provided near the reactor zone of the pretreatment reactor 10.

In general, the biomass will be treated in the pressurized pretreatment reactor 10 at an elevated temperature (e.g., above 185° C.) for a specific amount of time. In general, the temperature, pressure, and/or residence time of the biomass in the reaction zone may depend upon a number of variables, including the pH in the reaction zone and the degree of pretreatment. In one embodiment, the biomass has a residence time in the pretreatment reactor from about 10 seconds to about 20 minutes, or about 10 seconds to about 600 seconds. The pH for the pretreatment may be between about 0.5 and about 1.5, or between about 1.0 and about 1.5. Notably, the partially dewatered lignocellulosic feedstock may be heated prior to its entry into the reaction zone (e.g., in the optional heating chamber 4), in the reaction zone, or a combination thereof.

When the biomass has been resident in the reactor zone of the pretreatment reactor 10 for a predetermined time, the pretreated biomass is then discharged into a flash tank 20 to provide the pretreated biomass. Since the flash tank 20 is held at a pressure that is lower than the pressure of the pretreatment reactor 10, the temperature of the pretreated biomass will drop from the pretreatment temperature to a temperature dependent on the pressure in the flash tank.

The cooled, pretreated biomass composition produced by the pretreatment 10 and flashing 20 is fed to hydrolysis 30, followed by fermentation 40 and ethanol recovery (not shown). Depending on the temperature and/or pH of the cooled, pretreated biomass composition, it may be subjected to a temperature and/or pH adjustment (not shown). For example, in one embodiment, the cooled, pretreated biomass composition is actively cooled.

The flash stream exiting from the top of the flash tank 20 may include steam, gaseous sulfur dioxide, and/or other volatile compounds (e.g., which depend on the pressure of the flash tank). The flash stream is fed to a heat exchanger 61 which cools the flash stream, thereby providing a gaseous sulfur dioxide stream and a condensate 65. Advantageously, the heat exchanger also allows at least some of the heat/energy from the flash stream to be recycled. The gaseous sulfur dioxide stream is fed to a regenerative sulfur dioxide recovery unit 63. Regenerative sulfur dioxide recovery units, which may be amine-based, alkali-based, or based on another type of chemical/solvent, are known in the art. In many cases, regenerative sulfur dioxide recovery units include two column units, wherein the first column absorbs the sulfur dioxide and the second column regenerates the absorber and a sulfur dioxide stream. The use of a regenerative sulfur dioxide recovery unit may be advantageous if the flash stream contains a significant number of impurities (e.g., gases other than sulfur dioxide). Optionally, the sulfur dioxide recovered from the regenerative sulfur dioxide recovery is compressed and/or condensed, and recycled back into the process (e.g., fed to pretreatment).

One method of producing sulfur dioxide is to burn solid sulfur in a sulfur burner. For example, relatively high strength $SO_2$ gas (e.g., 18%) may be produced by burning sulfur in air, whereas even higher strength $SO_2$ gas may be produced using an oxy-fired system (e.g., where the sulfur is fired with cryogenic or pressure swing adsorption (PSA) pure oxygen). However, in order to avoid high furnace operating temperatures (e.g., which may form $NO_R$), a cold recycle gas typically is used. More specifically, a portion of the SO2 gas stream produced by the system is tapped, is cooled, and is redirected back to the sulfur furnace.

Figure 5:
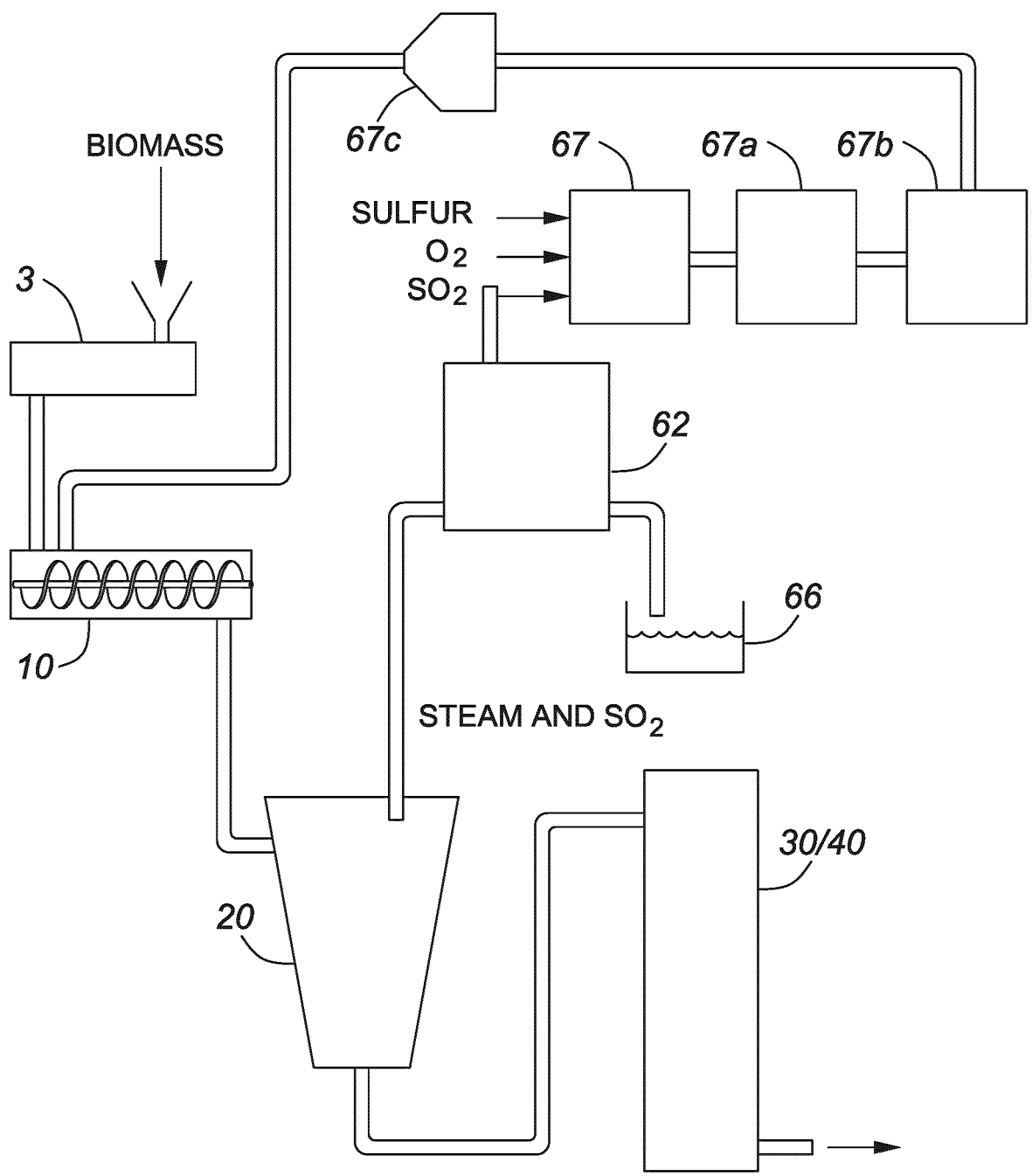
FIG. 5 is a schematic diagram showing a system for producing ethanol in accordance with another embodiment of the invention.

Referring to FIG. 5, there is shown one embodiment of a system including a sulfur dioxide recovery, wherein a flash stream obtained from the flashing step 20 is fed to a sulfur furnace 62 in order to avoid high furnace operating temperatures.

In operation, a slurry of lignocellulosic biomass having a consistency suitable for pretreatment is fed to the pretreatment reactor 10 via a conveyor 3. The pretreatment reactor 10, which for exemplary purposes is shown as a horizontal reactor, may be any reactor that may contain the biomass while the biomass is subject to at least a portion of the pretreatment. For example, in one embodiment, the pretreatment reactor is one of a plurality of pretreatment reactors. In one embodiment, the pretreatment reactor 10 may be equipped with an internal mechanism, such as a screw, conveyor, or similar mechanism, for conveying the lignocellulosic biomass within a reactor zone of the pretreatment reactor.

Sulfur dioxide and/or sulfurous acid is added to the pretreatment reactor 10 and/or the conveyor 3. For example, in one embodiment, the pretreatment reactor includes one or more inlets for injecting steam and/or sulfur dioxide/sulfurous acid into the biomass. Accordingly, the pretreatment reactor may be held at a predetermined temperature and/or pressure. In one embodiment, the one or more inlets for injecting steam are provided near the reactor zone of the pretreatment reactor 10.

In general, the biomass will be treated in the pressurized pretreatment reactor 10 at an elevated temperature (e.g., above 185° C.) for a specific amount of time. In general, the temperature, pressure, and/or residence time of the biomass in the reaction zone may depend upon a number of variables, including the pH in the reaction zone and the degree of pretreatment. In one embodiment, the biomass has a residence time in the pretreatment reactor from about 10 seconds to about 20 minutes, or about 10 seconds to about 600 seconds. The pH for the pretreatment may be between about 0.5 and about 1.5, or between about 1.0 and about 1.5.

When the biomass has been resident in the reactor zone of the pretreatment reactor 10 for a predetermined time, the pretreated biomass is then discharged into a flash tank 20 to provide the pretreated biomass. Since the flash tank 20 is held at a pressure that is lower than the pressure of the pretreatment reactor 10, the temperature of the pretreated biomass will drop from the pretreatment temperature to a temperature dependent on the pressure in the flash tank.

The cooled, pretreated biomass composition produced by the pretreatment 10 and flashing 20 is fed to hydrolysis 30, fermentation 40, and ethanol recovery (not shown). Depending on the temperature and/or pH of the cooled, pretreated biomass composition, it may be subjected to a temperature and/or pH adjustment (not shown). For example, in one embodiment, the cooled, pretreated biomass composition is actively cooled.

The flash stream exiting from the top of the flash tank 20 may include steam, gaseous sulfur dioxide, and/or other volatile compounds (e.g., which depend on the pressure of the flash tank). The flash stream is fed to a partial condenser 62, wherein it is cooled, thereby providing a stream comprising sulfur dioxide gas and a condensate 66.

The gaseous sulfur dioxide stream is fed to the sulfur furnace 67. More specifically, the stream comprising sulfur dioxide gas is used to maintain the temperature within the sulfur furnace, which burns sulfur with pure oxygen and/or air. The high strength sulfur dioxide gas produced by the furnace is cooled using a gas cooler or a waste heat boiler 67a, and is optionally passed through a gas cleaning unit 67b (e.g., an absorber tower circulating 98 wt % sulfuric acid). The sulfur dioxide gas exiting the gas cleaning unit 67b is compressed by compressor 67c and fed to the pretreatment reactor (e.g., directly or indirectly).

Advantageously, this configuration, which uses the cooled flash stream to manage the temperatures of the sulfur furnace 67, simplifies the sulfur burning process (i.e., since a separate cold recycle gas is not required to adjust the temperature of the sulfur burner), while also providing a method of recycling the sulfur dioxide in the flash stream. Furthermore, the sulfur furnace may destroy any volatile organics in the flash stream. Accordingly, a buildup of contaminants in the system and/or a need for a separate purification step may be avoided and/or reduced.

Further advantageously, this configuration may provide a relatively inexpensive method of recycling and/or providing sulfur dioxide for pretreatment. Although the sulfur burner may destroy volatile organics in the flash stream, in some embodiments, the system includes a condensation or other purification step for purging carbon dioxide and/or other inert compounds from the system, a sulfur dioxide drying step, a sulfur trioxide scrubber, and/or a sulfur dioxide scrubber for waste streams. Optionally, the sulfur dioxide gas provided by the compressor 67c is condensed and/or stored before being fed to the pretreatment reactor 10.

As discussed above, providing a system that includes sulfur dioxide recovery may facilitate processes that have a high equivalent sulfur dioxide loading (e.g., greater than about 10 wt %). Advantageously, pretreatment at temperatures over 185° C. and at a relatively high equivalent sulfur dioxide loading have been shown to provide a more effective hydrolysis. In particular, it has been found that equivalent sulfur dioxide loadings greater than about 10 wt %, and in particular greater than about 12 wt %, and/or at pH values less than 1.5 provide very efficient hydrolyses, particularly when compared to conventional sulfuric acid pretreatment. In general, an efficient hydrolysis may be recognized by a relatively high glucose conversion, the use of relatively less enzyme, and/or a relatively short hydrolysis time.

Figure 6:
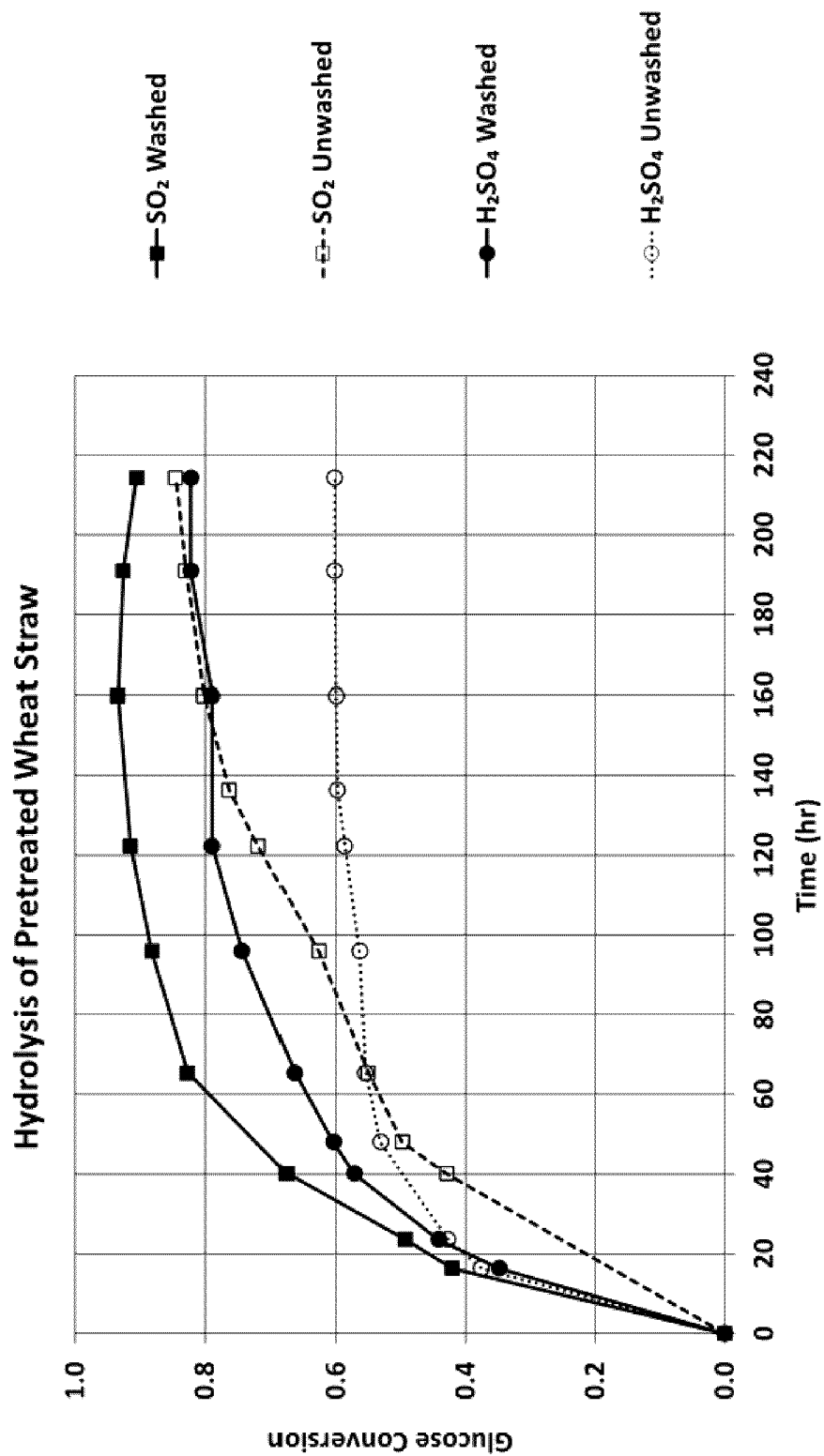
FIG. 6 is a plot of glucose conversion versus hydrolysis time for hydrolysis of $SO_2$ and $H_2SO_4$ catalyzed pretreated material.

A comparison of $SO_2$ catalyzed pretreatment conducted at an equivalent sulfur dioxide loading greater than about 10% relative to a conventional $H_2SO_4$ catalyzed pretreatment is provided in FIG. 6. More specifically, FIG. 6 shows the glucose conversion for washed and unwashed samples prepared by pretreating straw with $SO_2$ and for washed and unwashed samples prepared by pretreating straw with $H_2SO_4$. The preparation of the samples is discussed in the Examples. Referring again to FIG. 6, the glucose conversion achieved for $SO_2$ catalyzed pretreatment conducted at relatively high sulfur dioxide loading (e.g., $H_2SO_3$ washed) is higher than the glucose conversion achieved for conventional $H_2SO_4$ catalyzed pretreatment (e.g., $H_2SO_4$ washed), thus showing improved efficiency. Alternatively, or additionally, improved efficiency is recognized by the fact that the $SO_2$ catalyzed washed sampled reached 0.8 glucose conversion in about 60 hours, while the $H_2SO_4$ catalyzed washed sample took 160 hours to reach 0.8 glucose conversion.

Without being bound by theory, the improved hydrolysis efficiency is believed to be related to the high sulfur dioxide loading. For example, it has been found that the combination of a sulfur dioxide loading greater than about 10 wt % and a pretreatment temperature greater than about 180° C., or 185° C., may provide fewer and/or lower concentrations of contaminants, inhibitors, and/or inactivators for hydrolysis (e.g., the glucose conversion plateaus faster for the hydrolysis of $H_2SO_4$-catalyzed pretreated material than for $SO_2$-catalyzed pretreated material).

EXAMPLES

Example 1: $SO_2$ Catalyzed Pretreatment of Lignocellulosic Material

An $SO_2$ catalyzed batch pretreatment of wheat straw was conducted in 25 mL, stainless steel, laboratory tubular reactors (i.e., about 5 inches in length). The wheat straw was hammer-milled to provide an average particle size of ¼ inch-1 inch (0.635-2.54 cm) and had a cellulose/glucan content of 34.61%, xylan content of 20.09%, a lignin content of 20.49%, and a total solids (TS) content of 93.25%, w/w on a dry basis. The carbohydrate assay was based on Determination of Structural Carbohydrates and Lignin in Biomass-LAP (Technical Report NREL/TP-510-42618).

Each tubular reactor was charged with approximately 1.646 g of accurately weighed wheat straw and 3.47 mL of sulfurous acid solution (≥6% $H_2SO_3$, from Sigma-Aldrich), thus providing a slurry having a consistency of about 30 wt % and a pH of 1.1. Each tubular reactor was repeatedly shaken/inverted and then placed in an oil bath preheated to 195° C. The tubular reactor remained immersed in the oil bath for 5 minutes. At the end of the 5 minute pretreatment time, the tubular reactor was removed from the oil bath and placed in an ice bath for 5 minutes. The contents of the tubular reactors (e.g., pretreated material) were removed, weighed, and combined in a sealable plastic bag.

A portion of the pretreated material was removed for washing, to prepare a washed pretreatment sample for hydrolysis. Another portion of the pretreated material was removed to prepare an unwashed pretreatment sample for hydrolysis. The washed and unwashed samples were subject to enzymatic hydrolysis on the same day as the pretreatment.

A portion of the pretreated material was reserved to determine the undissolved solids (UDS) concentration, total solids (TS) concentration, dissolved solids (DS) concentration, and/or the concentration of monomeric sugars and/or degradation products.

More specifically, the filtrate from a portion of the $SO_2$ pretreated material was found to contain 9.77 g/L glucose, 75.42 g/L xylose, 0.21 g/L HMF and 4.36 g/L of furfural, using the method described in Example 6.

The carbohydrate content of the $SO_2$ pretreated material was ascertained with a carbohydrate assay based on Determination of Structural Carbohydrates and Lignin in Biomass-LAP (Technical Report NREL/TP-510-42618). The $SO_2$ pretreated material was found to contain 57.84% cellulose, 1.61% xylan and 27.88% insoluble lignin, w/w on a dry basis.

All experiments conducted with or based on $SO_2$/sulfurous acid are carried out in a fume hood, including the drying of samples for determining the dissolved solids and total solids concentrations.

Example 2: $H_2SO_4$ Catalyzed Pretreatment of Lignocellulosic Material

A $H_2SO_4$-catalyzed batch pretreatment of wheat straw was conducted in a 97 L steam gun, for comparison with the $SO_2$-catalyzed pretreatment. The wheat straw was hammer-milled to provide an average particle size of about ¼ inch-1 inch (0.635-2.54 cm) and had a cellulose/glucan content of 34.61%, a xylan content of 20.09%, a lignin content of 20.49%, and a total solids content of 89.5%, w/w on a dry basis.

To prepare for pretreatment, 400 g of the wheat straw was soaked overnight in a solution prepared from 22.3 mL of 96.5% $H_2SO_4$ and 6.72 L of water, thus providing a slurry having a consistency of about 5% and a pH of 1.30. Excess $H_2SO_4$ solution was drained from the wheat straw, which was then placed in a Bock basket centrifuge for 30 seconds. The centrifuged, $H_2SO_4$ soaked, lignocellulosic feedstock, which had a total solids (TS) concentration of 29.18%, was then stored at about 4° C.

The steam gun, which was preheated to 200° C., was charged with 1000 g of the centrifuged, $H_2SO_4$ soaked straw, which was cooked for 2 minutes. After 2 minutes, the steam gun was depressurized to 5 psi and the pretreated straw was removed from the steam gun. The pretreated material, which weighed 948.5 g and had a UDS of 19.63 wt %, was cooled before storage at about 4° C.

A portion of the pretreated material was removed for washing, to prepare a washed pretreatment sample for hydrolysis. Another portion of the pretreated material was removed to prepare an unwashed pretreatment sample for hydrolysis.

A portion of the pretreated material was reserved to determine the undissolved solids (UDS) concentration, total solids (TS) concentration, dissolved solids (DS) concentration, and/or the concentration of monomeric sugars and/or degradation products.

More specifically, the filtrate from a portion of the $H_2SO_4$ pretreated material contained 17.54 g/L glucose, 63.42 g/L xylose, 0.45 g/L HMF and 1.89 g/L of furfural.

The carbohydrate content of the $H_2SO_4$ pretreated material was ascertained with a carbohydrate assay based on Determination of Structural Carbohydrates and Lignin in Biomass-LAP (Technical Report NREL/TP-510-42618). The $H_2SO_4$ pretreated material was found to contain 54.33% cellulose, 1.40% xylan, and 29.72% insoluble lignin, w/w on a dry basis.

Example 3: Determination of Undissolved Solids Concentration

The determination of the undissolved solids (UDS) content, also referred to as the consistency, is carried out as follows. A fixed amount of a sample containing undissolved solids is dispensed into a plastic weigh dish and the weight is recorded accurately using an analytical scale. A glass microfiber filter paper circle of pore size 1.6 microns, appropriately sized for a Buchner funnel, is placed in an aluminum weighing tin and the combined weight of the tin and filter paper is recorded. After transferring the pre-weighed filter paper to the Buchner funnel, the pre-weighed sample is passed through the filter paper to isolate the solids. Small volumes of deionized water are used to ensure that the solids are quantitatively transferred from the weigh dish to the Buchner funnel. The solids are then washed using excess deionized water, after which the washed sample and filter paper are transferred into the pre-weighed aluminum tin. Care should be taken to ensure the solids are quantitatively transferred. After drying the aluminum tin in a 105° C. oven overnight, the contents are weighed accurately and the UDS is quantified by determining, as a percent, the number of grams of dry solids per gram of sample. UDS measurements are performed in duplicate and averaged.

UDS measurements are performed on unwashed pretreated samples to determine the amount of pretreated sample to add to the hydrolysis flask (e.g., using about 0.5 g aliquots).

Example 4: Measurement of Total Solids Concentration in a Pretreated Feedstock Composition The determination of the total solids (TS) content is carried out as follows. A fixed amount of a sample is dispensed into a pre-weighed aluminum tin (if sample is washed) or crucible (if sample is unwashed). After drying the aluminum tin/crucible in a 105° C. oven or muffle furnace (disposed in a fume hood) overnight, the contents are weighed accurately and the total solids are quantified by determining, as a percent, the number of grams of dry solids per gram of sample. TS measurements are performed in duplicate and averaged.

TS measurements are performed on washed pretreated samples to determine the amount of pretreated sample to add to the hydrolysis flask (e.g., using about 0.5 g aliquots).

TS measurements are performed on unwashed pretreated samples as an alternate method for determining dissolved solids.

Example 5: Measurement of Dissolved Solids Concentration in a Pretreated Feedstock Composition The determination of the dissolved solids concentration of a pretreated feedstock composition is carried out as follows. A glass microfiber filter paper circle of pore size 1.6 microns that has not been pre-wetted is placed in a Buchner funnel. A sample of a pretreated feedstock composition is applied to the filter paper and filtered by vacuum. The filtrate is collected and weighed into a pre-weighed crucible. After drying the crucible in a 105° C. muffle furnace (placed in a fume hood) overnight, the contents are weighed accurately and the concentration of dissolved solids is quantified by determining, as a percent, the number of grams of dry solids per gram of filtrate.

Alternatively, the concentration of dissolved solids (% DS) is obtained from $$\% \, DS = \% \, TS - \% \, UDS \quad (3)$$

Example 6: Determination of the Concentration of Monomeric Sugars and/or Degradation Products Determination of the concentration of monomeric sugars and/or degradation products, such as furans, was achieved using high performance liquid chromatography (HPLC).

The sugar composition (e.g., concentration of glucose and/or xylose) of pretreated material and/or of aliquots from the enzymatic hydrolysis was determined using a Dionex ICS-3000 ion chromatography system equipped with an electrochemical detector (ED40) with gold electrode. Separation was performed on a CarboPac™ PA1 column (4×250 mm) and a PA1 guard column (4×50 mm). The detector temperature and column temperature were both 30° C. NaOH (10 and 200 mM solutions) was used as an eluent at a flow rate of 1.5 mL/min. All sample injection volumes were 25 µL. Sugar concentrations were calculated by comparison to standard sugar samples containing arabinose, galactose, glucose, xylose and cellobiose (Certified from Absolute Standards).

Concentration of furans (e.g., concentration of 5-(hydroxymethyl)furfural (HMF) and/or furfural) in the pretreated material and/or in aliquots from the enzymatic hydrolysis were determined using a Dionex ICS-3000 ion chromatography system equipped with a Dionex AD25 Absorbance detector set at 278 nm. Separation was performed on a Varian Microsorb-MV C18 (4×250 mm) and Phenomenex Security guard column with Carbo-H cartridges. Detector temperature and column temperature were both 30° C. A solution of 5:95 (v/v) ACN:deionized water was used as an eluent at a flow rate of 1 mL/min. All sample injection volumes were 25 µL. Furan concentrations were calculated by comparison to standard furan samples containing 5-(Hydroxymethyl)furfural (HMF), furfuryl alcohol, and furfural (Certified from Absolute Standards).

The filtrate from a portion of the $SO_2$ pretreated material was found to contain 9.77 g/L glucose, 75.42 g/L xylose, 0.21 g/L HMF, and 4.36 g/L of furfural.

The filtrate from a portion of the $H_2SO_4$ pretreated material was found to contain 17.54 g/L glucose, 63.42 g/L xylose, 0.45 g/L HMF, and 1.89 g/L of furfural.

Example 7: Preparation of the Washed Pretreatment Samples for Hydrolysis

Washed pretreatment samples were prepared by suspending a portion of pretreated sample in ultra-purified water (Milli-Q™) in an approximately 1:1 (v/v) ratio, filtering the suspension through glass fiber filter paper (G6, 1.6 microns), and then repeating the alternating steps of adding the same volume of ultra-purified water (Milli-Q™) to the pretreated solids followed by filtration through the glass fiber filter paper, another eight times.

The washed pretreatment solids were added to a pre-weighed 50 mL Erlenmeyer flask, in an amount selected to provide a consistency of about 10 wt % for hydrolysis (e.g., corresponding to about 1 g of dry pretreated material for a total weight of the flask contents, including the enzyme, of 10 g). To determine the amount of wet, washed pretreatment solids that corresponds to 1 g of dry pretreatment material, 1 g is divided by the total solids (TS) of the washed pretreated sample.

In the washed $SO_2$ catalyzed pretreatment samples prepared according to Examples 1 and 7, the TS was found to be 21.43%, thus providing a target weight of wet slurry to be added to the Erlenmeyer flask of 4.6662 g.

Once an accurately weighed amount of washed pretreatment solids (target weight of 4.6662 g) has been added to the Erlenmeyer, 0.420 mL sodium citrate (2.38 M of citrate buffer pH adjusted to 5.2) was added to the flask (e.g., an amount selected to provide a target 100 mM concentration once enzyme). Ultra-purified water (Milli-Q™) was then added to bring the flask contents up to a target weight, predetermined to bring the final weight of the contents to 10 g once enzyme is added. The flasks were incubated at 52° C., with moderate shaking at about 250 rpm, for 30 minutes to equilibrate substrate temperature.

Example 8: Preparation of the Unwashed Pretreatment Samples for Hydrolysis

Unwashed pretreatment samples were prepared by adjusting the pH of a portion of the as-is pretreated material to about 5 by adding a solution of 30% lime ($Ca(OH)_2$) in small increments. The pH-adjusted pretreatment material was then added to a pre-weighed 50 mL Erlenmeyer flask, in an amount selected to provide a consistency of about 10 wt % for hydrolysis (e.g., corresponding to about 1 g of dry pretreated material for a total weight of the flask contents, including the enzyme, of 10 g). To determine the amount of pretreated slurry that corresponds to 1 g of dry pretreatment material, 1 g is divided by the UDS of the pH adjusted pretreated sample.

In the unwashed SO$_2$ catalyzed pretreatment samples prepared according to Example 1, the UDS of the pH-adjusted pretreated sample was found to be 17.42%, thus providing a target weight of wet slurry to be added to the Erlenmeyer flask of 5.7389 g.

Once an accurately weighed amount of unwashed slurry (target weight of 5.7389 g) has been added to the Erlenmeyer, 0.420 mL of 2.38 M sodium citrate buffer (prepared by adjusting the pH of citric acid monohydrate to about 5.2 with 30% NaOH) was added to the flask (e.g., an amount selected to provide a target 100 mM concentration once enzyme). Ultra-purified water (Milli-Q™) was then added to bring the flask contents up to a target weight, predetermined to bring the final weight of the contents to 10 g once enzyme is added. The flasks were incubated at 52° C., in an orbital shaker (250 rpm), for 30 minutes to equilibrate substrate temperature.

Example 9: Enzymatic Hydrolysis of Pretreated Samples

Hydrolysis was initiated by adding liquid cellulase enzyme to the Erlenmeyer flasks prepared in Examples 7 and 8 (i.e., containing the pretreated material, citrate buffer, and make-up water), thus bringing the total content weight up to 10 g. Enzyme was added at 5 mg/g, 7 mg/g, and 9 mg/g (i.e., mg protein/g of cellulose enzyme loading). The flasks were incubated at 52° C. in an orbital shaker (250 rpm) for 215 hours.

The pH of the washed samples were maintained at about 5 (e.g., between 4.8 and 5.2) for the duration of the hydrolysis by the citrate buffer. The pH of the unwashed samples were periodically adjusted to 5 (i.e., twice a day for the first 72 hours of hydrolysis, and once a day for the remaining duration of the hydrolysis). The pH was adjusted by adding a solution of 30% lime (Ca(OH)$_2$) in 10 µL increments. The volume of pH adjusting solution added was recorded, and used to adjust total volume when calculating cellulose conversion.

The hydrolyses were followed by measuring the sugar monomers in the hydrolysate. More specifically, aliquots obtained at 16, 24, 40, 48, 60, and 72 hours of hydrolysis, and at 24 hours intervals after the 72 hours, were used to analyze the sugar content. Each aliquot was obtained at the specific time interval by swirling the flask, withdrawing 200 µL of the flask contents with a wide-bore pipette tip and depositing it in a 1.5 mL Eppendorf centrifuge tube, placing the centrifuge tube in a boiling water for 10 minutes to deactivate the enzyme, and storing the aliquot at about 4° C. for subsequent sugar analysis.

To assay samples for monomeric sugars, the samples were warmed to room temperature and were centrifuged for 4 minutes at 14,800 rpm. The supernatant was diluted in water for measuring the glucose with the HPLC, and were measured using the method in Example 6.

Since the slurries in the hydrolysis flasks were too thick at time 0 hours, the glucose measurements at time 0 hours was calculated using the glucose concentration measured for the corresponding filtrate, the enzyme solution glucose contribution, and the total volume of the contents of the corresponding hydrolysis flask, which includes volume added from the lime addition, buffer solution, make-up water, and enzyme addition.

The glucose conversion was determined assuming:

$$\text{Maximum glucose} = \left( \frac{\text{g of dry substrate} * \% \text{cellulose in the substrate}}{\text{aqueous volume }(L)} \right) * 2 \left( \frac{180.1559 \text{ g/mol}}{324.28 \text{ g/mol}} \right) \quad (4)$$

$$\text{Glucose conversion} = \frac{\text{concentration of glucose in aliquot}}{\text{maximum glucose}} \quad (5)$$

The results are presented in FIG. 6. More specifically, FIG. 6 shows a plot of glucose conversion as a function of time for both washed and unwashed samples, for both SO$_2$ and H$_2$SO$_4$ catalyzed pretreatments, with a 5 mg/g enzyme loading.

Referring to the assays referred to in Examples 1 and 2, the SO$_2$ catalyzed pretreatment resulted in more cellulose (e.g., 57.84% compared to 54.22%), more xylan (1.61% compared to 1.40%), and less insoluble lignin (e.g., 27.88% compared to 29.72%), relative to the H$_2$SO$_4$ catalyzed pretreatment. In addition, the filtrate from the SO$_2$ catalyzed pretreatment resulted in less glucose (9.77 g/L compared to 17.54 gL), more xylose (75.42 g/L compared to 63.42 g/L), less HMF (0.21 g/L compared to 0.45 g/L), and more furfural (4.36 g/L compared to 1.89 g/L), relative to the H$_2$SO$_4$ catalyzed pretreatment.

Referring to FIG. 6, hydrolysis of the SO$_2$ catalyzed pretreatment washed sample reached about 0.9 glucose conversion at 160 hours, whereas hydrolysis of the H$_2$SO$_4$ catalyzed pretreatment washed sample only reached 0.8 glucose conversion at 160 hours. By comparison, hydrolysis of the SO$_2$ catalyzed pretreatment unwashed sample reached 0.8 glucose conversion at 160 hours, whereas hydrolysis of the H$_2$SO$_4$ catalyzed pretreatment unwashed sample only reached 0.6 glucose conversion at 160 hours.

Although the hydrolysis of each washed pretreated material was generally more efficient than the hydrolysis of the corresponding unwashed pretreated material, the surprising result is that the hydrolysis of the unwashed SO$_2$ catalyzed pretreatment material reached substantially the same, or higher, glucose conversion as the hydrolysis of the washed H$_2$SO$_4$ catalyzed pretreatment material at times over 160 hours. In particular, even though the hydrolysis of the unwashed SO$_2$ catalyzed pretreatment material started out relatively slowly (e.g., even slow relative to the hydrolysis of the unwashed H$_2$SO$_4$ catalyzed pretreatment material), with time it eventually surpassed the glucose conversion obtained by hydrolysis of the washed H$_2$SO$_4$ catalyzed pretreatment material. Accordingly, without being bound by theory, it does not appear that there is a high concentration of inactivating compounds in the unwashed SO$_2$ catalyzed pretreatment material (e.g., for comparison, the hydrolysis of the H$_2$SO$_4$ catalyzed pretreatment material plateaus around 0.6, thus indicating at least some inactivation of the enzyme).

Advantageously, since the hydrolysis of the unwashed SO$_2$ catalyzed pretreatment material reached substantially the same, or a higher, glucose conversion as the hydrolysis of the washed H$_2$SO$_4$ catalyzed pretreatment material, the SO$_2$ catalyzed pretreatment may provide a reasonable alternative to H$_2$SO$_4$ catalyzed pretreatment, even when the pretreated material is not washed and/or diluted before being fed to hydrolysis. Although the cost of SO$_2$ catalyzed pretreatment may be more than the cost of H$_2$SO$_4$ catalyzed pretreatment (e.g., due to the cost of SO$_2$ compared to $H_2SO_4$, and due to the required equipment, including $SO_2$ recovery) this cost may be offset by providing little to no washing and by the reduction in the amount of enzyme required. For example, preliminary experiments have indicated that $SO_2$ pretreatment may use less than 50% of the enzyme conventionally used for hydrolyzing $H_2SO_4$ catalyzed pretreated materials, while still providing a high glucose conversion. In addition, since the $SO_2$ may be recovered in a sulfur recovery unit, the costs may be further reduced.

In general, an efficient hydrolysis may exploit a relatively high glucose conversion, use less enzyme, and/or have shorter hydrolysis times. For example, referring again to FIG. 6, high efficiency hydrolysis of $SO_2$ catalyzed pretreated material is demonstrated by the high glucose conversion of the $SO_2$ washed sample, and/or by the fact that the $SO_2$ catalyzed washed sampled reached 0.8 glucose conversion in about 60 hours, while the $H_2SO_4$ catalyzed washed sample took 160 hours to reach 0.8 glucose conversion.

Figure 7:
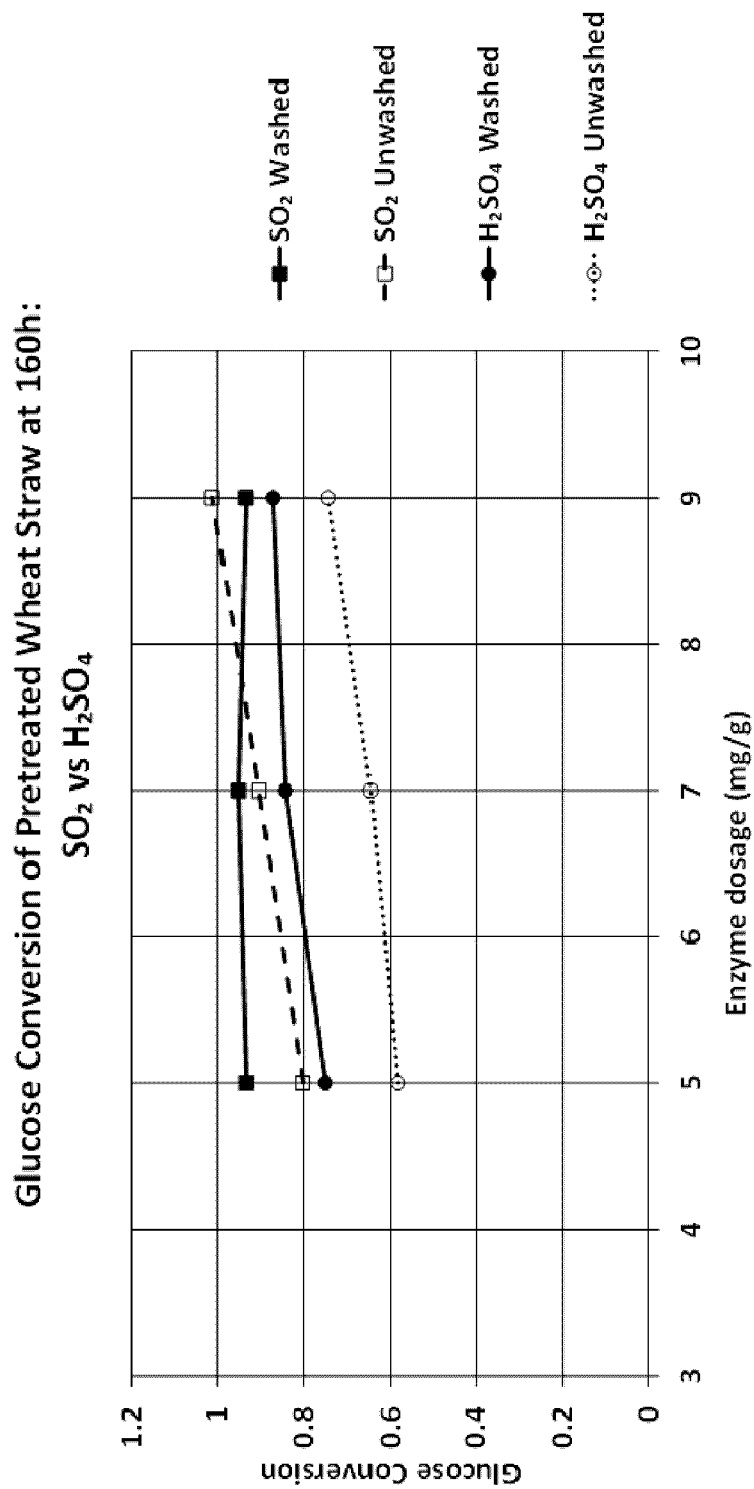
FIG. 7 is a plot of glucose conversion versus enzyme dosage for hydrolysis of $SO_2$ and $H_2SO_4$ catalyzed pretreated material.

Referring to FIG. 7, there is shown a plot of glucose conversion as a function of enzyme dosage (e.g., 5 mg/g, 7 mg/g, and 9 mg/g) measured from aliquots removed at time equal to 160 hours of hydrolysis, for both the washed and unwashed samples. Referring to the $H_2SO_4$ catalyzed pretreated washed and unwashed samples, a glucose conversion of about 0.75 requires almost twice the amount of enzyme for the unwashed sample (e.g. about 9 mg/g) as for the washed sample (e.g., about 5 mg/g). In contrast, referring to the $SO_2$ catalyzed pretreated washed and unwashed samples, a glucose conversion of at least 0.9 may be achieved using similar enzyme dosages for both the unwashed sample (e.g. about 8 mg/g) and the washed sample (e.g., about 8 mg/g). In this case, high efficiency of the hydrolysis is demonstrated by the fact that the enzymatic hydrolysis of the unwashed $SO_2$ catalyzed pretreated material with cellulase enzymes, performs almost as well as a hydrolysis conducted on the washed pretreated feedstock composition produced by the same pretreatment. In addition, high efficiency is demonstrated by the fact that a glucose conversion greater than about 0.9 may be obtained for the unwashed $SO_2$ catalyzed sample at an enzyme dosage of only 7 mg/g at 160 hours. In contrast, a similar glucose conversion level with the washed $H_2SO_4$ catalyzed sample requires a larger enzyme dosage (e.g., greater than 9 mg/g). Accordingly, a process that includes no or little washing/dilution of the pretreated material, and that requires less enzyme (e.g., relative to a conventional $H_2SO_4$ catalyzed pretreatment) may be provided.

Example 10: Determining the Amount of Potentially Available Xylose

The determination of the amount of potentially available xylose is carried out as follows. The xylan content was determined using a carbohydrate assay based on Determination of Structural Carbohydrates and Lignin in Biomass-LAP (Technical Report NREL/TP-510-42618).

By knowing the xylan content of the feedstock, the potentially available xylose is calculated using the following:

$$P = X_f U_s * 1.14 * D_s / (1 - (1 - X_f) U_s) \quad (6)$$

where P=Potentially available xylose (g/L), $X_f$=Xylan concentration in feedstock (%), $U_s$=UDS of pretreated slurry (%), and $D_s$=Density of pretreated slurry (g/L). The factor 1.14 accounts for the hydration of xylan to xylose. The factor $1/(1-(1-X_f)U_s)$ accounts for the volume occupied by undissolved solids, excluding xylan.

This concentration of potentially available xylose, P, may be compared to the concentration of xylose measured using HPLC found in the sulfur dioxide pretreated biomass composition to provide the percentage of potentially available xylose.

For example, if the feedstock slurry is 15% UDS, the feedstock is 20% xylan, the pretreated slurry density is 1030 g/L, the potentially available xylose is calculated as:

(20%)(15%)(1.14)(1030)/(1−(1−20%)(15%))=40.03 g/L

If the xylose concentration in the sulfur dioxide and/or sulfurous acid pretreated slurry is 31.20 g/L, the percentage of potentially available xylose is (31.20)/(40.03)*100=77.9%.

Example 11: $SO_2$ Flashing Following Pretreatment of Lignocellulosic Material

An $SO_2$ catalyzed batch pretreatment of wheat straw was conducted in a 25 mL laboratory tubular reactor. The reactor was formed from a stainless steel tube (i.e., about 5 inches in length and about 9/16 inch internal diameter). One end of the tube was secured with a hex Swagelok fitting and cap. The other end of the tube was provided with a valve and piping, where the valve is operable between an open position, wherein there is fluid communication between the tube and the piping, and a closed position wherein there is no fluid communication between the tube and the piping. The valve is a needle valve formed from stainless steel (severe service). The piping is formed of stainless steel (i.e., having an outer diameter of ⅛ inch and an inner diameter of 0.028 inch) and is bent and/or curved to direct any gas escaping through the piping, when the valve is open, into a container.

The wheat straw was hammer-milled to provide an average particle size of about ¼ inch (0.635 cm) and had a glucan content of 34.61% and a total solids (TS) content of 91.6%, w/w on a dry basis. The carbohydrate assay used to determine the glucan content was based on Determination of Structural Carbohydrates and Lignin in Biomass-LAP (Technical Report NREL/TP-510-42618).

The tubular reactor was charged (e.g., with the valve removed) with approximately 1.5 g of accurately weighed wheat straw (dry) and 3.35 mL of sulfurous acid solution (≥6% $H_2SO_3$, from Sigma-Aldrich), and the reactor sealed with the valve closed.

The tubular reactor was placed in a 26 L oil bath preheated to 195° C., where it remained submerged (except for the valve and piping) for 5 minutes. At the end of the 5 minute pretreatment, the tubular reactor was removed from the oil bath and the distal tip of the metal tubing was positioned into a bottle containing a premeasured mass of 5% hydrogen peroxide solution such that the distal end of the metal tubing was below the liquid level (i.e., while the contents of the tubular reactor were still hot). The reactor valve was then opened to release the pressure and left open until the unit was at ambient pressure. The valve was then closed and the reactor placed into an ice bath to cool.

Recalling that sulfur dioxide dissolves and/or reacts with water to form sulfurous acid according to

$$SO_{2(g)} + H_2O_{(l)} = H_2SO_3 \quad (7)$$

and that sulfurous acid may be oxidized to sulfuric acid by the peroxide according to

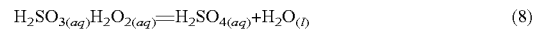
$$H_2SO_{3(aq)} + H_2O_{2(aq)} = H_2SO_{4(aq)} + H_2O_{(l)} \quad (8)$$

the amount of sulfur dioxide vented from the tubular reactor can be determined using the difference in mass of the peroxide solution before and after venting. Accordingly, the mass of the collection vessel was measured to give the total mass of the solution for calculation purposes. In particular, assuming the collection solution has a density of about 1 g/mL, the total volume of the collection solution in mL is equal the total mass of collection solution in grams.

The concentration of $SO_4^{2-}$ in the peroxide solution was determined using HPLC. More specifically, an aliquot of the peroxide collection liquor was taken and diluted appropriately. The diluted sample was analyzed with a Metrohm 881 Compact IC pro HPLC, equipped with a conductivity detector, an A-supp 5 column, and a guard column with suppressed conductivity.

The percentage of sulfur dioxide that flashed at the end of the pretreatment is determined as follows:

$$\% \; SO2 \; \text{flashed} = \frac{g \; SO2 \; \text{flashed}}{g \; SO2 \; \text{initial}} \; \text{where} \quad (9)$$

$$g \; SO2 \; \text{flashed} = \frac{g \; SO4}{MM SO4} * MM SO2 \quad (10)$$

$$g \; SO4 = [SO4] \; \text{in collection} \quad (11)$$
$$\text{solution}(g/L) * \text{volume collection solution} \; (L)$$

$$g \; SO2 \; \text{inital} = \quad (12)$$
$$\text{volume } H2SO3 \; (mL) \; \text{added to reactor} * \frac{6 \; g}{100 \; mL} * \frac{MM \; SO2}{MM H2SO3}$$

In order to determine the quantity of free $SO_2$ remaining in the pretreated slurry, 10 mL of 1% hydrogen peroxide (i.e., 2 mL 5% hydrogen peroxide and 8 mL water) was added to the cooled pretreated slurry. The pretreated slurry was mixed and allowed to stand for several minutes. The concentration of $SO_2$ in the solution was determined using HPLC. In particular, an aliquot was removed from the pretreated slurry, was syringe filtered, and diluted appropriately. The diluted sample was analyzed with a Metrohm 881 Compact IC pro HPLC, equipped with a conductivity detector, an A-supp 5 column, and a guard column with suppressed conductivity. The eluent was an aqueous carbonate solution.

The percentage of $SO_2$ that remained in the pretreated slurry following flashing relative to the initial amount of $SO_2$ was determined as follows:

$$\% \; SO_2 \; \text{flashed} = \frac{g \; SO2 \; \text{remaining}}{g \; SO2 \; \text{initial}} \; \text{where} \quad (13)$$

$$gSO2 \; \text{remaining} = \quad (14)$$
$$\left([SO4] \; \text{in solution} \left(\frac{g}{L}\right) * \text{total volume of liquid for analysis}(L)\right) *$$
$$\frac{MM \; SO2}{MM \; SO4}$$

total volume of liquid for analysis = (15)
liquid remaining after flashing (mL) + 10 mL peroxide solution liquid remaining after flashing (mL) = (16)
total liquid before flashing(mL) − liquid lost during flashing (mL)

total liquid before flashing (mL) = total liquid added (mL) + (17)
(dry straw mass (g) − (dry straw mass (g) * UDS))

total liquid added (mL) = acid added (mL) + water content of straw (18)

Figure 8:
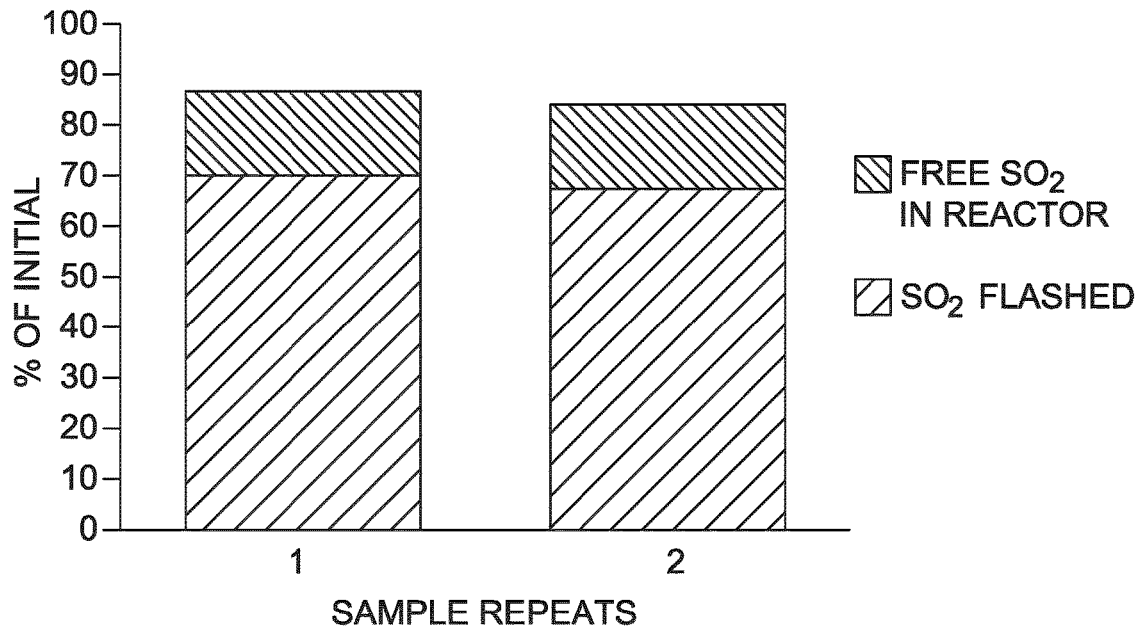
FIG. 8 is a bar graph showing the percentage of $SO_2$ flashed and the percentage of $SO_2$ remaining in the pretreatment reactor after flashing, relative to the initial $SO_2$ added.

UDS = undissolved solids remaining after pretreatment (19)

liquid lost during flashing (mL) = (20)
(mass of collection flask after flash(g) −
mass of collection flask before flash(g)) * 1 mL/g The results are illustrated in FIG. 8. More specifically, FIG. 8 shows the percentage of sulfur dioxide that remained in the pretreated slurry following flashing (i.e., labeled free $SO_2$ in reactor) and the percentage of sulfur dioxide that flashed (i.e., labeled $SO_2$ flashed), for two different samples. More specifically, FIG. 8 shows that the average percentage of $SO_2$ that flashed was about 70%, the average percentage of $SO_2$ that remained in the slurry was about 18%, leaving about 12% that may form lignosulfonates and/or is otherwise consumed.

Notably, this relatively large percentage of flashed $SO_2$ resulted when the equivalent sulfur dioxide loading is relatively large (e.g., greater than 10%). In particular, the equivalent sulfur dioxide loading for the pretreatment of 1.5 g (dry) of wheat straw with 3.35 mL 6 wt % sulfurous acid is approximately 10.4%. Accordingly, it has been shown that sulfur loadings greater than about 10% may allow about 70% of the initially introduced sulfur dioxide to be flashed and collected after pretreatment. Accordingly, significant cost savings may be achieved.

Figure 9:
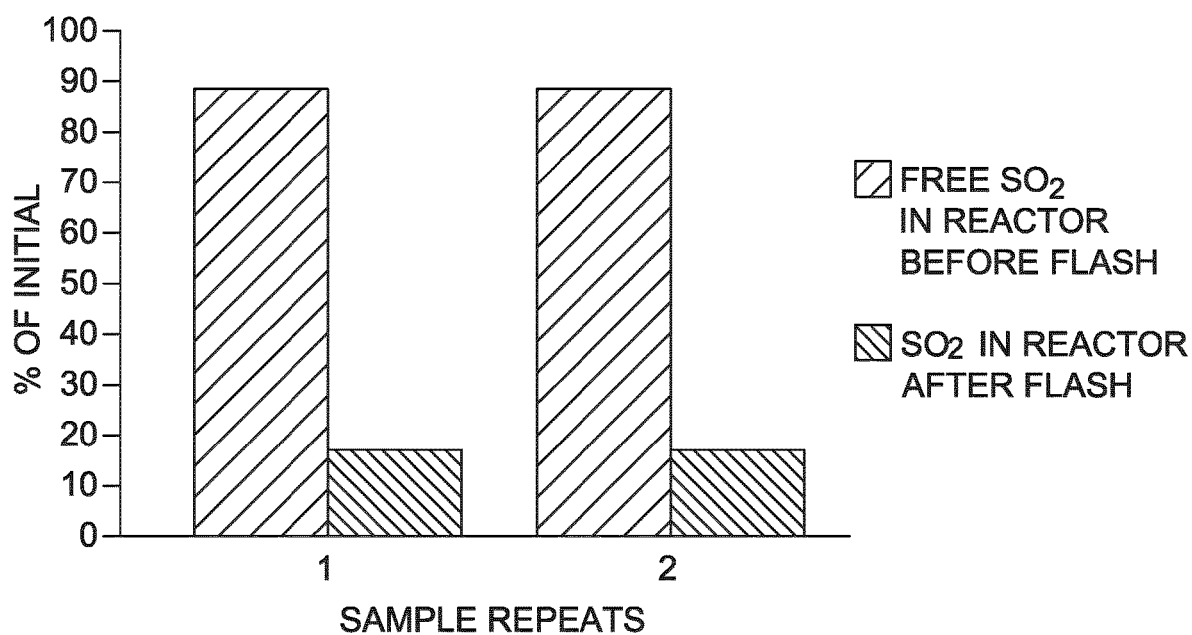
FIG. 9 is a bar graph showing the percentage of $SO_2$ in the pretreatment reactor before flashing and the percentage of $SO_2$ remaining in the pretreatment reactor after flashing.

Referring to FIG. 9, there is shown a bar graph illustrating the difference between the percentage of sulfur dioxide that was found in the pretreated slurry before flashing (i.e., labeled free $SO_2$ in reactor before flash) and the percentage of sulfur dioxide that was found in the pretreated slurry after flashing (i.e., labeled free $SO_2$ in reactor after flash), for two different samples. More specifically, FIG. 9 shows that the difference between these two values is approximately 70% (i.e., the percentage of initial $SO_2$ found to have flashed).

In order to determine the free $SO_2$ in reactor before flash, a separate experiment was conducted wherein an accurately weighed amount of the same wheat straw (i.e., target weight of 1.5 g dry) and 3.35 mL of sulfurous acid solution (≥6% $H_2SO_3$, from Sigma-Aldrich) was placed in a tubular reactor that was not equipped with a valve/piping. The tubular reactor was placed in a 26 L oil bath preheated to 195° C., where it remained submerged for 5 minutes. At the end of the 5 minute pretreatment time, the tubular reactor was placed in an ice bath for 5 minutes.

In order to determine the quantity of free $SO_2$ remaining in the pretreated slurry, 10 mL of 1% hydrogen peroxide solution was added to the cooled pretreated slurry. The pretreated slurry was mixed and allowed to stand for several minutes. The concentration of $SO_2$ in the solution was determined using HPLC. In particular, an aliquot was removed from the pretreated slurry, was syringe filtered, and diluted appropriately. The diluted sample was analyzed with a Metrohm 881 Compact IC pro HPLC, equipped with a conductivity detector, an A-supp 5 column, and a guard column with suppressed conductivity. The eluent was an aqueous carbonate solution.

The percentage of sulfur dioxide that was in the reactor before flashing (i.e., but after pretreatment) was determined as follows:

$$\% \; SO2 \; \text{in reactor before flash} = \frac{gSO2 \; \text{after pretreatment}}{gSO2 \; \text{initial}} \; \text{where} \quad (21)$$

$$gSO2 \; \text{after pretreatment} = \quad (22)$$
$$\left([SO4] \; \text{in peroxide after pretreatment}\left(\frac{g}{L}\right) * \text{aqueous volume} \; (L)\right) *$$
$$\frac{MM \; SO2}{MM \; SO4}$$

aqueous volume = (23)
total liquid added (mL) + 10 mL peroxide solution +
(straw mass (g) − (straw mass (g) * UDS))

Referring to FIG. 9, most of the free $SO_2$ determined to be in the slurry before flashing, flashes off during the pressure reduction. Accordingly, a large percentage (e.g., greater than 30%, 50%, 60%, or 70%) of the unreacted $SO_2/H_2SO_3$ may be advantageously collected, recovered, and/or recycled back in the process. Moreover, a large percentage (e.g., greater than 30%, 50%, 60%, or 70%) of the initial $SO_2$/$H_2SO_3$ may be advantageously collected, recovered, and/or recycled back in the process.

Example 12: Determining the Glucan, Xylan, and Lignin Content

As described above, the cellulose/glucan content, xylan content, and/or lignin content discussed in Examples, 1, 2, 10, and 11, was determined by a carbohydrate assay based on Determination of Structural Carbohydrates and Lignin in Biomass-LAP (Technical Report NREL/TP-510-42618). In particular, the carbohydrate assay was modified specifically for wheat straw and/or pretreated wheat straw. For example, the wheat straw sample was treated with 69 wt % sulfuric acid, wherein 1.5 mL of sulfuric acid is provided per 0.15 g of sample. The sample was incubated in a water bath at 50° C. for 30 minutes. An additional 43.5 mL water was added to provide an acid concentration of about 3.6 wt % $H_2SO_4$. The sample was then set in an autoclave set at 116° C. for 50 minutes. Once the sample was cooled, the determination of carbohydrate content, and in particular the sugar monomers, was determined using high performance liquid chromatograph (HPLC). A sugar recovery standard (SRS) containing known concentrations of arabinose, galactose, glucose, xylose, and 3.6 wt % $H_2SO_4$ was also placed in an autoclave set 116° C. for 50 minutes. The determination of sugar monomers in the SRS was used to correct for losses due to decomposition of the sugars. In particular, the corrected xylan and/or glucan content was determined using the following equation:

$$\frac{Carbohydrate_{corrected}(mg)}{fiber\ g} = \frac{\frac{monomeric\ sugar_{HPLC}(g/L)}{\%\ R_{srs}/100} \times Volume\ Diluted\ (mL) \times MW\ ratio}{Wt\ of\ sample(g) \times \%\ total\ solids\ content} \times 100\ where \qquad (24)$$

$$\%\ R_{SRS} = \frac{(C_{sugar\ HPLC}(g/L)\ in\ SRS)_{autoclaved}}{(C_{sugar_{HPLC}}(g/L)\ in\ SRS)_{nonautoclaved}} \times 100, \qquad (25)$$

$\%\ R_{SRS} =$
Percent recovery for individual sugar in sugar recovery standard
$C_{sugar} =$ Concentration of individual sugar, and
MW ratio = molecular weight ratio of polymeric
sugar ($C_5$ or $C_6$) to monomeric sugar ($C_5$ or $C_6$)

For calculating xylan content, $$MW\ ratio = \qquad (26)$$
$$\frac{MW\ repeating\ unit}{2 \times MW\ C5} = \frac{MW\ C_{10}H_{16}O_8}{2 \times MW\ C_5H_{10}O_5} = \frac{264.23}{2 \times 150.13} = 0.88$$

For calculating glucan content, $$MW\ ratio = \qquad (27)$$
$$\frac{MW\ repeating\ unit}{2 \times MW\ C_6} = \frac{MW\ C_{12}H_{20}O_{10}}{2 \times MW\ C_6H_{12}O_6} = \frac{324.28}{2 \times 180.15} = 0.90$$

The calculated lignin content corresponds to the acid-insoluble lignin.

Of course, the above embodiments have been provided as examples only. It will be appreciated by those of ordinary skill in the art that various modifications, alternate configurations, and/or equivalents will be employed without departing from the spirit and scope of the invention. For example, while the above-described embodiments focus on the recovery of sulfur dioxide from the flash stream, other embodiments additionally provide sulfur recovery from other points in the process. For example, in one embodiment, sulfur bound to the lignin and/or sulfur that forms sulfonic acids is recovered in a separate step, and depending upon whether sulfur dioxide is liberated, may be combined with the sulfur dioxide recovered from the flash stream. Accordingly, the scope of the invention is therefore intended to be limited solely by the scope of the appended claims.

The invention claimed is:

1. A process for producing ethanol from lignocellulosic biomass comprising:
  a) adding acid to lignocellulosic biomass to produce acidified lignocellulosic biomass, said acid comprising at least one of sulfur dioxide and sulfurous acid;
  b) pretreating said acidified lignocellulosic biomass to produce a pretreated biomass composition comprising cellulose and xylose, said pretreating conducted in a pressurized pretreatment reactor at a temperature above 185° C. and at a pH less than 1.5;
  c) reducing a pressure on the pretreated biomass composition to produce a flash stream and a cooled pretreated biomass composition;
  d) obtaining at least one of sulfur dioxide and sulfurous acid from at least one of the flash stream and a stream derived from the flash stream;
  e) hydrolyzing cellulose from the cooled pretreated biomass composition in the presence of a cellulase to produce glucose;
  f) fermenting at least a portion of the glucose to ethanol; and
  g) recycling the at least one of sulfur dioxide and sulfurous acid derived from step d) back into the process, wherein said acid is added in an amount equivalent to provide at least 15% weight sulfur dioxide on weight of dry lignocellulosic biomass.

2. The process according to claim 1, wherein step a) includes adding sulfur dioxide upstream of the pretreatment, during the pretreatment, or a combination thereof.

3. The process according to claim 1, wherein a residence time of the acidified lignocellulosic biomass in the pretreatment reactor is less than 8 minutes.

4. The process according to claim 1, wherein the cellulase is provided at a concentration less than 12 milligrams protein per gram of cellulose.

5. The process according to claim 1, wherein the pH is less than 1.25.

6. The process according to claim 1, wherein d) comprises recovering sulfur dioxide from the flash stream.

7. The process according to claim 1, wherein d) comprises collecting gaseous sulfur dioxide from the flash stream.

8. The process according to claim 7, wherein d) comprises at least one of condensing and absorbing the collected gaseous sulfur dioxide.

9. The process according to claim 7, wherein d) comprises feeding the flash stream to a partial condenser that provides a first stream comprising a condensate and a second stream comprising gaseous sulfur dioxide.

10. The process according to claim 9, comprising feeding the condensate to a sulfur dioxide stripper.

11. The process according to claim 9, comprising compressing the stream comprising gaseous sulfur dioxide.

12. The process according to claim 9, comprising dissolving the gaseous sulfur dioxide in water to form a sulfurous acid solution.

13. The process according to claim 1, wherein d) comprises feeding the at least one of the flash stream and the stream derived from the flash stream to a sulfur dioxide recovery unit.

14. The process according to claim 1, wherein g) comprises adding recycled sulfur dioxide to the lignocellulosic biomass in the pretreatment, upstream of the pretreatment, or a combination thereof.

15. The process according to claim 1, wherein pretreating comprises adding steam to the acidified lignocellulosic biomass in the pretreatment reactor, upstream of the pretreatment reactor, or a combination thereof, to provide the temperature of at least 185° C.

16. The process according to claim 1, wherein steam and the acid are added to the lignocellulosic biomass in a vessel upstream of the pretreatment reactor.

17. The process according to claim 1, wherein the pretreating is conducted in a reactor wherein a ratio of volume of vapour space to volume of lignocellulosic biomass is between 1 and 10.

18. The process according to claim 1, wherein the cellulose in step e) has not been washed.

19. The process according to claim 1, wherein step e) comprises feeding at least a portion of the cooled pretreated biomass composition to a hydrolysis tank such that at least 50% of the xylose produced in step b) enters the hydrolysis tank.

20. The process according to claim 1, wherein the pretreating is conducted on lignocellulosic biomass having a consistency between 15 wt % and 40 wt %.

21. The process according to claim 1, comprising feeding at least one of the flash stream and a stream derived from the flash stream to a partial condenser.

22. The process according to claim 1, comprising feeding at least one of the flash stream and a stream derived from the flash stream to a sulfur burner.

23. The process according to claim 1, wherein the pretreating in step (b) comprises pretreating without adding a volatile solvent.

24. The process according to claim 4, wherein the cellulose in step e) has not been washed.

25. The process according to claim 4, wherein step e) comprises feeding at least a portion of the cooled pretreated biomass composition to a hydrolysis tank such that at least 50% of the xylose produced in step b) enters the hydrolysis tank.

26. The process according to claim 1, wherein said pretreating comprises an acid-catalyzed steam pretreatment.

27. The process according to claim 1, wherein said pretreating is conducted in the absence of ethanol.

\* \* \* \* \*